United States Patent
Maggard et al.

(10) Patent No.: US 10,098,767 B2
(45) Date of Patent: Oct. 16, 2018

(54) RECONFIGURABLE STENT-GRAFT DELIVERY SYSTEM AND METHOD OF USE

(75) Inventors: Jason Maggard, Santa Rosa, CA (US); Jeffery Argentine, Petaluma, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 1165 days.

(21) Appl. No.: 13/457,544

(22) Filed: Apr. 27, 2012

(65) Prior Publication Data
US 2013/0289693 A1    Oct. 31, 2013

(51) Int. Cl.
*A61F 2/95* (2013.01)
*A61F 2/06* (2013.01)
(Continued)

(52) U.S. Cl.
CPC ........ *A61F 2/95* (2013.01); *A61F 2002/9517* (2013.01); *A61M 39/0606* (2013.01);
(Continued)

(58) Field of Classification Search
CPC .......... A61M 39/0693; A61M 39/0606; A61M 2039/0673; A61M 39/10; A61M 39/105; A61M 39/14; A61M 2039/1061; A61M 2039/1066; A61M 2039/1072; A61M 2039/1077; A61M 2039/1083;
(Continued)

(56) References Cited

U.S. PATENT DOCUMENTS

| 5,195,980 A | * | 3/1993 | Catlin | ............... A61M 39/0693 604/167.04 |
| 5,425,765 A | | 6/1995 | Tiefenbrun et al. | |

(Continued)

FOREIGN PATENT DOCUMENTS

| EP | 0875262 | 11/1998 |
| JP | 2007/181702 | 7/2007 |

(Continued)

OTHER PUBLICATIONS

Bungay et al. "Initial Experience With a New Fenestrated Stent Graft" Journal of Vascular Surgery, 2011, pp. 1-7.
(Continued)

*Primary Examiner* — Julian W Woo
(74) *Attorney, Agent, or Firm* — Medler Ferro Woodhouse & Mills PLLC

(57) ABSTRACT

A reconfigurable delivery system is disclosed having a multi-lumen delivery catheter configuration that permits the delivery and staged release of a self-expanding main vessel stent-graft and a delivery sheath configuration that permits the introduction of various medical devices for the delivery and implantation of various branch vessel stent-grafts that are to be mated with the main vessel stent-graft. A method is disclosed wherein the delivery system is first used in the multi-lumen delivery catheter configuration to deliver and release a main vessel stent-graft that is configured for placement in the abdominal aorta for treatment of short-neck infrarenal, juxtarenal, and/or suprarenal aneurysms and then used in the delivery sheath configuration to facilitate the delivery of branch vessel stent-grafts that are configured to extend from the main vessel stent-graft into a respective renal artery.

18 Claims, 29 Drawing Sheets

(51) Int. Cl.
  *A61M 39/06* (2006.01)
  *A61M 39/08* (2006.01)
(52) U.S. Cl.
  CPC ............ *A61M 2039/062* (2013.01); *A61M 2039/0646* (2013.01); *A61M 2039/082* (2013.01)
(58) Field of Classification Search
  CPC ........ A61M 2039/188; A61M 39/0613; A61M 39/08; A61M 2039/062; A61M 2039/0686; A61M 2039/082; A61M 2039/064; A61M 2039/0646; A61M 2039/0653; A61M 2039/066; A61M 2039/0666; A61M 25/00; A61M 25/0014; A61M 25/0015; A61M 25/0052; A61M 25/0097; A61M 2025/0004; A61M 2025/0006; A61M 2025/0034; A61M 2025/0036; A61M 2025/0035; A61M 2025/0037; A61M 2025/004; A61M 25/0172; A61M 25/0662; A61M 2025/0681; A61M 25/09041; A61M 25/0905; A61F 2/95; A61F 2/02; A61F 2/06; A61F 2/07; A61F 2/954; A61F 2/958; A61F 2/96; A61F 2/962; A61F 2/966; A61F 2/2427; A61F 2/243; A61F 2/2433; A61F 2/2436; A61F 2/2439; A61F 2/97; A61F 2002/9505; A61F 2002/9511; A61F 2002/9517; A61F 2002/061; A61F 2002/075; A61F 2002/9665; A61F 2002/011; A61F 2/852; A61F 2002/072; A61F 2002/077; A61F 2002/823; A61F 2002/826; A61F 2002/828; A61F 2002/9522; A61F 3/00; Y10S 623/902
  USPC .................................................. 623/1.11, 1.12
  See application file for complete search history.

(56) References Cited

U.S. PATENT DOCUMENTS

| | | | |
|---|---|---|---|
| 5,617,878 A | 4/1997 | Taheri | |
| 5,782,904 A | 7/1998 | White et al. | |
| 5,911,710 A * | 6/1999 | Barry | A61M 39/0693 604/167.04 |
| 6,042,605 A | 3/2000 | Martin et al. | |
| 6,352,553 B1 | 3/2002 | Van der Burg et al. | |
| 6,352,561 B1 | 3/2002 | Leopold et al. | |
| 6,361,637 B2 | 3/2002 | Martin et al. | |
| 6,379,365 B1 * | 4/2002 | Diaz | A61F 2/958 606/108 |
| 6,471,722 B1 | 10/2002 | Inoue | |
| 6,520,986 B2 | 2/2003 | Martin et al. | |
| 6,524,335 B1 | 2/2003 | Hartley et al. | |
| 6,551,350 B1 | 4/2003 | Thornton et al. | |
| 7,131,991 B2 | 11/2006 | Zarins et al. | |
| 7,306,623 B2 | 12/2007 | Watson | |
| 7,413,573 B2 | 8/2008 | Hartley et al. | |
| 7,438,721 B2 | 10/2008 | Doig et al. | |
| 7,537,606 B2 | 5/2009 | Hartley et al. | |
| 7,678,141 B2 | 3/2010 | Greenan et al. | |
| 7,682,380 B2 | 3/2010 | Thornton et al. | |
| 7,736,571 B2 | 6/2010 | Trapp | |
| 7,867,270 B2 | 1/2011 | Hartley et al. | |
| 7,955,374 B2 | 6/2011 | Erickson et al. | |
| 8,216,295 B2 * | 7/2012 | Benjamin | A61F 2/95 623/1.11 |
| 2005/0027345 A1 * | 2/2005 | Horan | A61F 2/013 623/1.12 |
| 2005/0256461 A1 * | 11/2005 | DiFiore | A61M 25/0075 604/247 |
| 2007/0055360 A1 | 3/2007 | Hanson et al. | |
| 2007/0083215 A1 | 4/2007 | Hamer et al. | |
| 2007/0156224 A1 | 7/2007 | Cioanta et al. | |
| 2007/0208256 A1 | 9/2007 | Marilla | |
| 2007/0225797 A1 | 9/2007 | Krivoruchko | |
| 2007/0233220 A1 | 10/2007 | Greenan | |
| 2007/0244547 A1 | 10/2007 | Greenan | |
| 2007/0250152 A1 | 10/2007 | Xiao et al. | |
| 2008/0287920 A1 * | 11/2008 | Fangrow | A61M 39/1011 604/535 |
| 2008/0294234 A1 | 11/2008 | Hartley et al. | |
| 2008/0306469 A1 * | 12/2008 | Masuda | A61M 39/045 604/535 |
| 2009/0204202 A1 | 8/2009 | Dierking et al. | |
| 2010/0004730 A1 | 1/2010 | Benjamin et al. | |
| 2011/0118816 A1 | 5/2011 | Jensen et al. | |
| 2011/0125244 A1 | 5/2011 | Roeder et al. | |
| 2011/0125249 A1 | 5/2011 | Jensen et al. | |
| 2011/0190868 A1 | 8/2011 | Ducke et al. | |
| 2012/0010692 A1 * | 1/2012 | Frye et al. | 623/1.11 |
| 2012/0035714 A1 | 2/2012 | Ducke et al. | |
| 2012/0046728 A1 | 2/2012 | Huser et al. | |

FOREIGN PATENT DOCUMENTS

| | | |
|---|---|---|
| JP | 2009-511123 | 3/2009 |
| JP | 2009-532111 | 9/2009 |
| WO | WO01/17587 | 3/2001 |
| WO | WO2010/002931 | 1/2010 |
| WO | WO2011/140583 | 11/2011 |

OTHER PUBLICATIONS

1st Japanese Office Action, JP Appln No. 2015-508947, dated Dec. 19, 2016.

Japanese Patent Application No. 2015-508949, 1st Office Action dated Jan. 4, 2017, pp. 1-4.

* cited by examiner

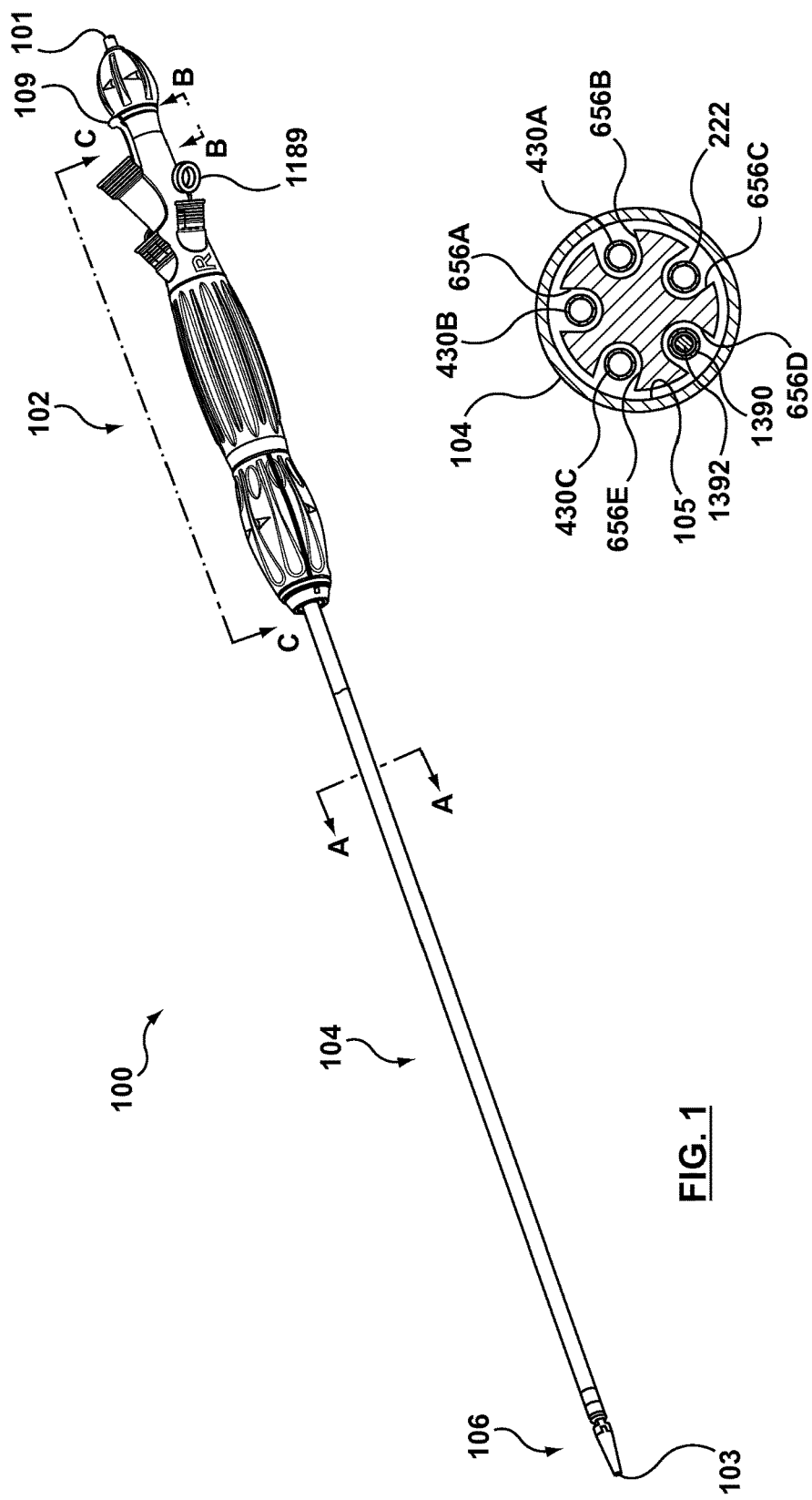

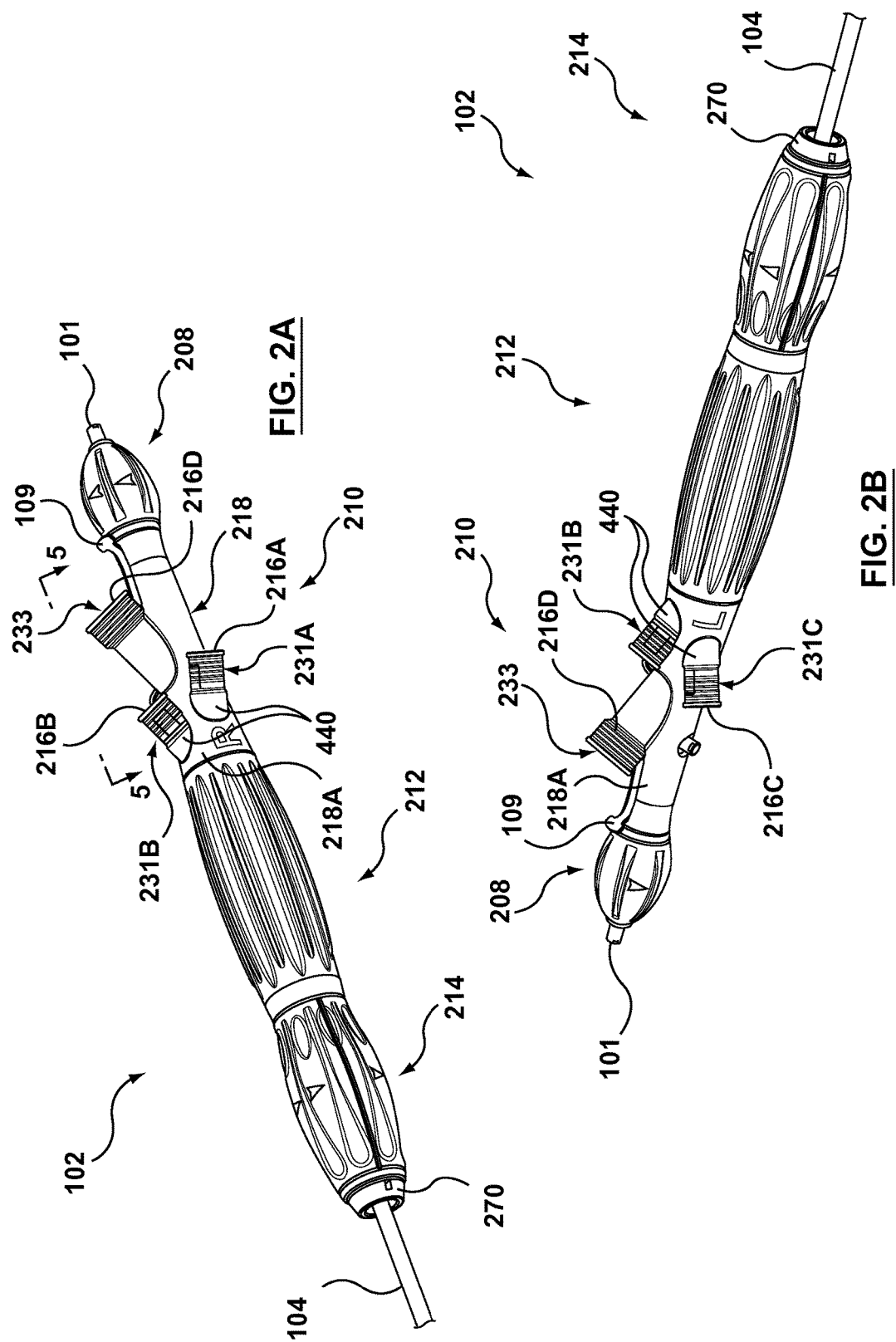

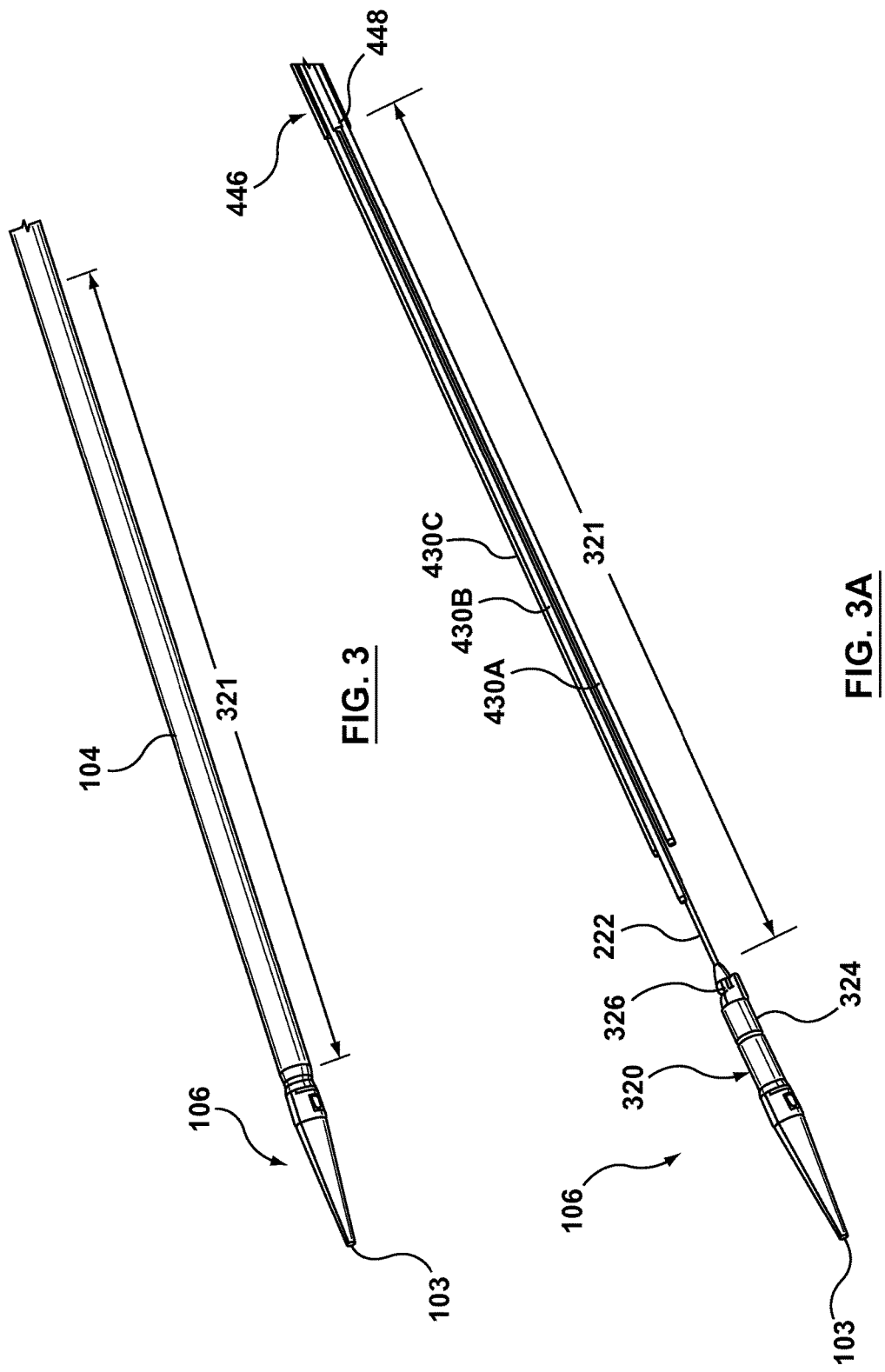

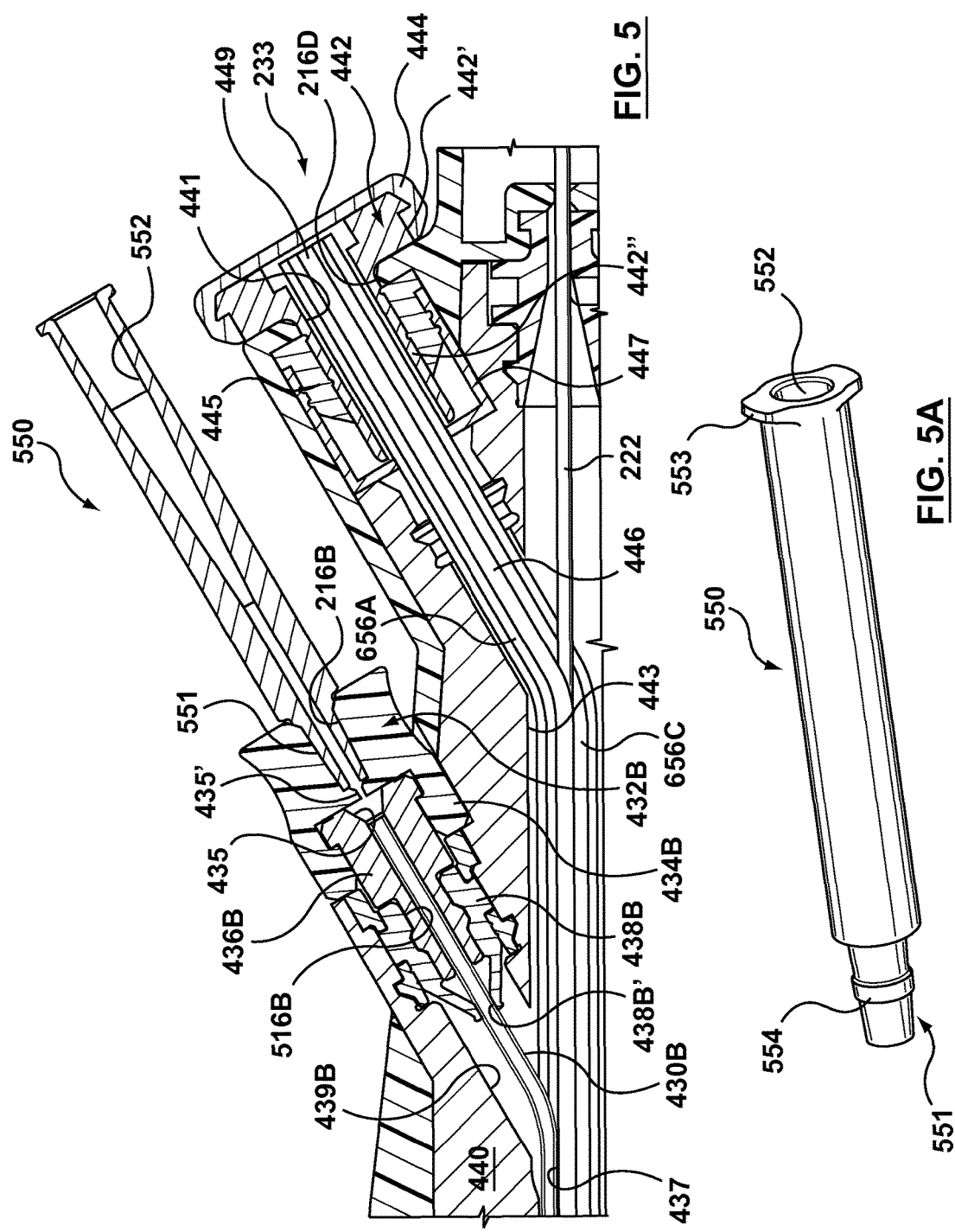

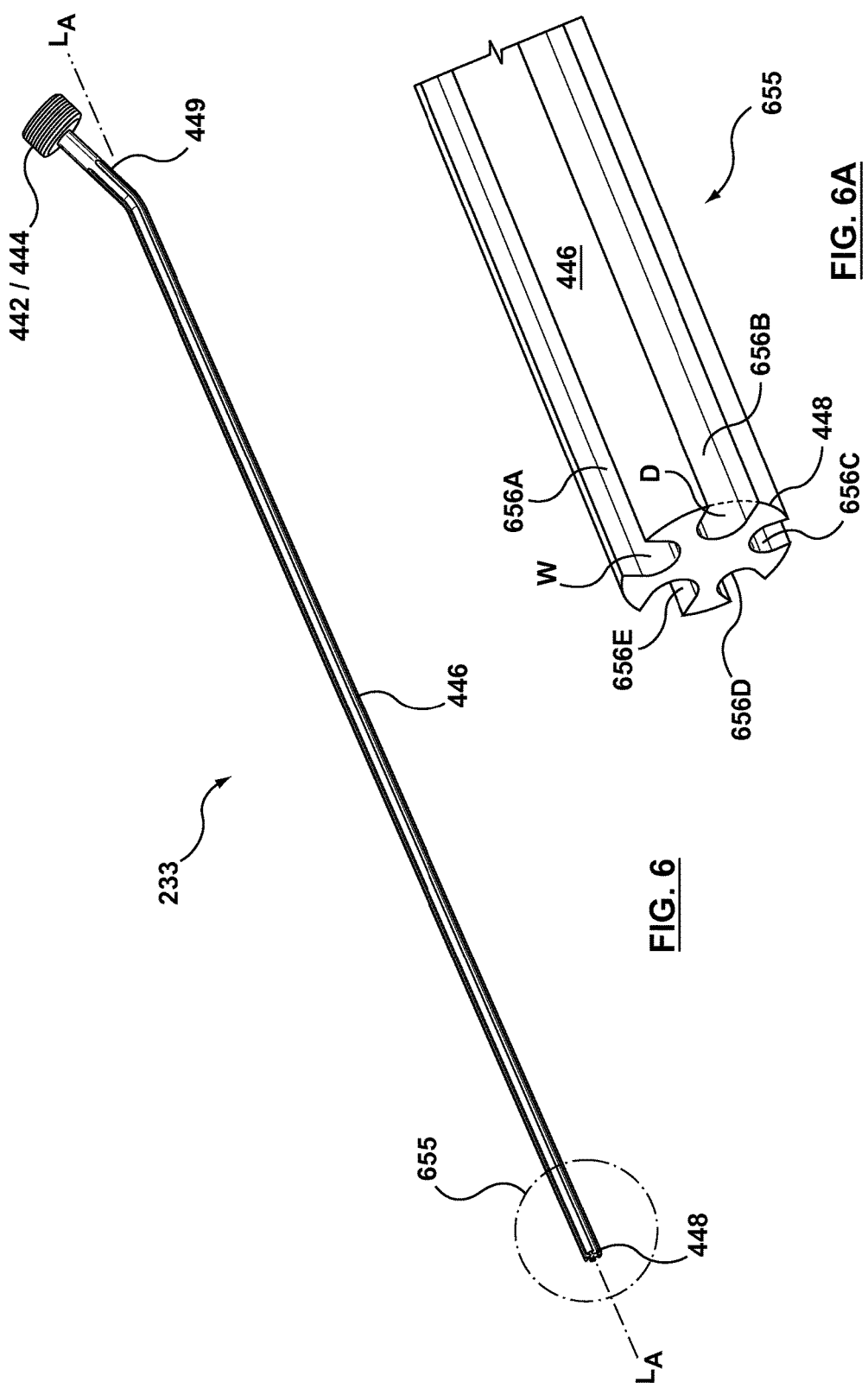

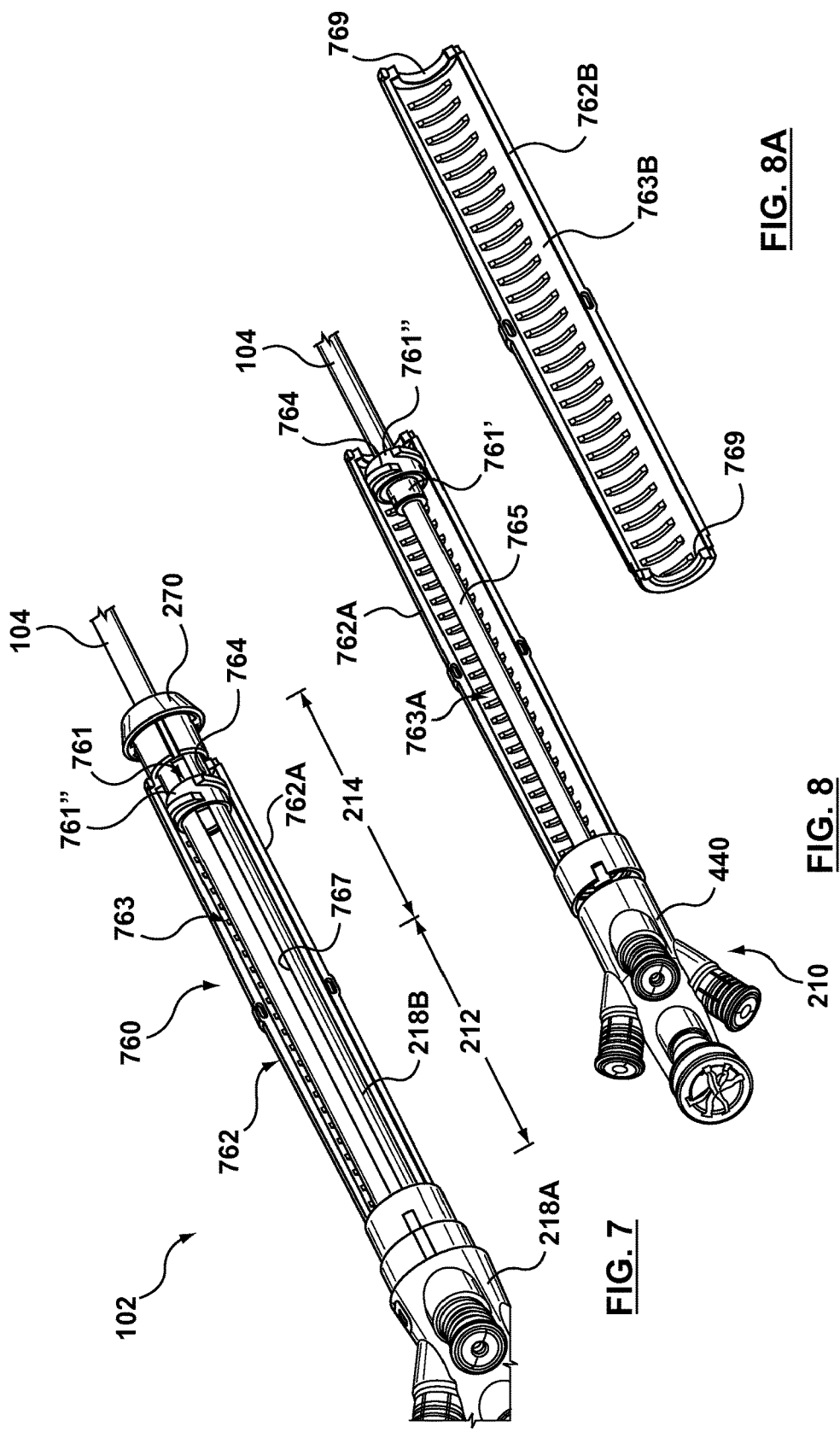

RECONFIGURABLE STENT-GRAFT DELIVERY SYSTEM AND METHOD OF USE

FIELD OF THE INVENTION

The invention relates to stent-graft delivery systems and more particularly to a stent-graft delivery system for delivering and implanting mating stent-graft segments.

BACKGROUND OF THE INVENTION

Tubular prostheses, such as stents, grafts, and stent-grafts are known for treating abnormalities in various passageways of the human body. In vascular applications, these devices often are used to replace or bypass occluded, diseased or damaged blood vessels such as stenotic or aneurysmal vessels. For example, it is well known to use stent-grafts of a biocompatible graft material supported by a framework, for e.g., one or more stent or stent-like structures, to treat or isolate aneurysms. The framework provides mechanical support and the graft material or liner provides a blood barrier. When implanting a stent-graft, the stent-graft typically is placed so that one end of the stent-graft is situated proximal to or upstream of the diseased portion of the vessel and the other end of the stent-graft is situated distal to or downstream of the diseased portion of the vessel. In this manner, the stent-graft extends through and spans the aneurysmal sac and extends beyond the proximal and distal ends thereof to replace or bypass the dilated wall.

Such tubular prostheses are known to be implanted in either an open surgical procedure or by a minimally invasive endovascular approach. Minimally invasive endovascular stent-grafts for use in treating aneurysms are often preferred over traditional open surgery techniques where the diseased vessel is surgically opened, and a graft is sutured into position bypassing the aneurysm. The endovascular approach generally involves opening a vein or artery with a needle, inserting a guidewire into the vein or artery through the lumen of the needle, withdrawing the needle, inserting over the guidewire a dilator located inside an associated sheath introducer having a hemostasis valve, removing the dilator and inserting a delivery catheter through the hemostasis valve and sheath introducer into the blood vessel. The delivery catheter with the stent-graft secured therein may then be routed through the vasculature to the target site. For example, a stent-graft delivery catheter loaded with a stent-graft can be percutaneously introduced into the vasculature, for e.g., into a femoral artery, and the stent-graft delivered endovascularly across an aneurysm where it is then deployed.

Specialized endovascular stent-grafts have been developed for the treatment of abdominal aortic aneurysm, hereinafter referred to as an AAA. An AAA is a bulge that forms in the wall of the abdominal aorta, which is the main vessel of the arterial system of the body that extends through the abdomen. An endovascular stent-graft for use in the abdominal aorta typically includes a number of self-expanding stent-graft segments that are assembled or mated within the patient to provide the finished stent-graft implant. The stent-graft implant may include a main stent-graft segment that constitutes a trunk section with two descending limb sections with the limb sections providing an anchoring point for subsequent endovascular placement of a right iliac limb stent-graft segment and a left iliac limb stent-graft segment of the stent-graft implant. Typically, the main stent-graft segment is delivered and implanted via a main delivery system that is withdrawn prior to respective branch delivery systems being introduced for delivery and implantation of each of the iliac limb stent-graft segments.

Although the endovascular approach is much less invasive, usually requiring less recovery time and involving less risk of complication as compared to open surgery, there can be concerns with anchoring and alignment of prostheses in relatively complex AAA applications such as ones involving branch vessels. The procedure becomes more complicated and the number of interventional devices needed to complete the procedure increases when more than one branch vessel is treated. For example, an AAA may occur having a proximal neck that is diseased or damaged to the extent that it cannot support an effective seal and connection with a prosthesis, such as is the case with short neck infrarenal, juxtarenal and suprarenal aneurysms. In some such presentations, a main stent-graft segment is provided with fenestrations or openings formed in its side wall below an upstream end thereof and in addition to iliac limb stent-graft segments being needed to complete the stent-graft implant, branch stent-graft segments are also used that extend between a respective fenestration of the main stent-graft segment and its branch vessel. To ensure alignment of the main stent-graft segment's fenestrations and the branch vessels, current techniques involve placing guidewires through each fenestration and branch vessel, e.g., each renal artery, prior to releasing the main stent-graft segment. Thereafter, branch delivery systems are introduced to deliver the branch stent-graft segments between the main stent-graft segment and the respective branch vessel with additional delivery systems then being introduced to deliver the iliac limb stent-graft segments between the main stent-graft segment and their respective vessels. A consequence of current treatments for AAA with the delivery of multiple stent-grafts that mate together to form a partial or complete implant are lengthy procedure times and the potential for patient harm that may be associated with delivery of the multiple interventional devices that are currently necessary to perform the delivery, positioning and assembly of the stent-graft segments.

What is needed in treating an AAA located at or about branch vessels is a simplified method for delivering the multiple mating stent-graft segments that eliminates procedure steps associated with the cannulation of mating features on the main stent-graft segment as well as a delivery system that can serve multiple functions to reduce the number of additional interventional devices needed to perform the procedure.

BRIEF SUMMARY OF THE INVENTION

Embodiments hereof are directed to a reconfigurable delivery system having a multi-lumen delivery catheter configuration and a delivery sheath configuration. When configured as a multi-lumen delivery catheter the delivery system permits the delivery and staged release of a self-expanding main vessel stent-graft. When configured as a delivery sheath, the delivery system permits the introduction of various medical devices for the delivery and implantation of various branch vessel stent-grafts that are to be mated with the main vessel stent-graft.

Another embodiment hereof is directed to a method of using the delivery system. The delivery system is first used in the multi-lumen delivery catheter configuration for delivering and staging the release of a main vessel stent-graft that is configured for placement in the abdominal aorta for treatment of short-neck infrarenal, juxtarenal, and/or suprarenal aneurysms. The delivery system is then used in the delivery sheath configuration for introducing medical devices that deliver branch vessel stent-grafts, which are configured to extend from the main vessel stent-graft into respective renal arteries.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a perspective view of a reconfigurable delivery system in accordance with an embodiment hereof.

FIG. 1A is a cross-sectional view of the delivery system shown in FIG. 1 taken long line A-A.

FIGS. 2A and 2B are enlarged alternate views of a handle component of the delivery system shown in FIG. 1.

FIG. 3 is an enlarged view of a distal portion of the delivery system shown in FIG. 1.

FIG. 3A depicts the distal portion of the delivery system shown in FIG. 3 with a sheath component proximally retracted to expose a tip capture mechanism of a distal tip assembly in accordance with an embodiment hereof.

FIG. 5 is a sectional view of the port section of the handle component of FIG. 2A taken along line 5-5.

FIG. 5A is a side view of an access seal dilator shown in FIG. 5 in accordance with an embodiment hereof.

FIG. 6 is a perspective view of a middle member component removed from the delivery system shown in FIG. 1 in accordance with an embodiment hereof.

FIG. 6A is an enlarged view of a distal portion of the middle member component shown in FIG. 6.

FIGS. 7, 8, 8A and 8B are various views of a portion of the delivery system of FIG. 1 with a main grip section and a driver grip section of a handle component partially disassembled in accordance with an embodiment hereof.

DETAILED DESCRIPTION OF THE INVENTION

Specific embodiments of the present invention are now described with reference to the figures, wherein like reference numbers indicate identical or functionally similar elements. Regarding "proximal" and "distal" positions referenced herein, a proximal end of a prosthesis, e.g., stent-graft, is the end closest to the heart by way of blood flow path whereas a distal end of the prosthesis is the end furthest away from the heart during deployment. In contrast, a distal end of the stent-graft delivery system or other associated delivery apparatus is usually identified as the end that is farthest from the operator, while a proximal end of the delivery system and devices is the end nearest the operator or handle of the catheter. In addition, the term "self-expanding" is used in the following description with reference to one or more stent structures of the prostheses hereof and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely exemplary in nature and is not intended to limit the invention or the application and uses of the invention. Although the description of embodiments hereof are in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

Figure 1B:
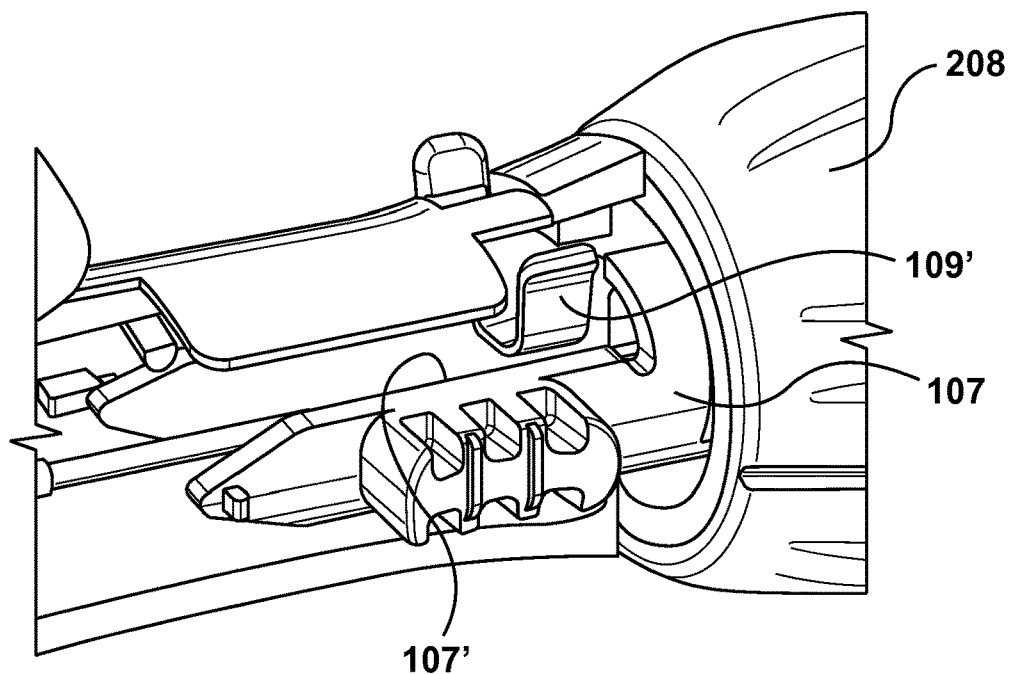
FIG. 1B is a sectional view of the delivery system shown in FIG. 1 taken long line B-B.
Figure 1C:
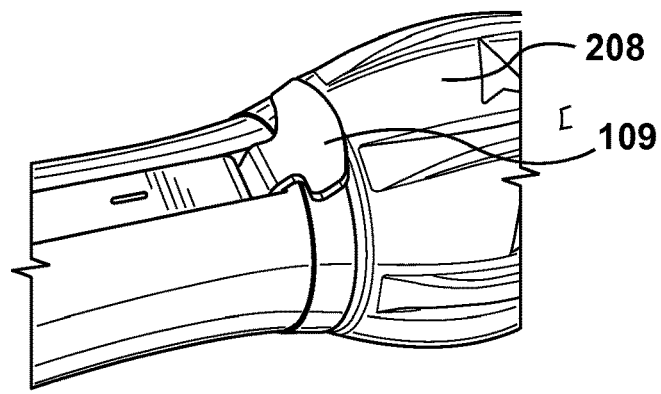
FIG. 1C is an enlarged view of a trigger wire pull tab of a handle component of the delivery system shown in FIG. 1.

FIG. 1 is a perspective view of a reconfigurable delivery system 100 for use in treating an abdominal aortic aneurysm that occurs at branch vessels in accordance with an embodiment hereof, with FIGS. 2A, 2B and 3 being enlarged views of proximal and distal portions of the delivery system, respectively. In an embodiment described herein, delivery system 100 may be initially configured in a multi-lumen delivery catheter configuration to deliver a self-expanding main stent-graft to the treatment site within the aorta and then re-configured to a delivery sheath configuration to permit subsequent branch delivery catheters and other medical devices to be introduced and deployed between the main stent-graft and the branch vessels.

Delivery system 100 includes a handle component 102, a sheath or outer tubular component 104, and a distal tip assembly 106. Handle component 102 is disposed at a proximal end of delivery system 100 and, with reference to FIGS. 2A-2C, includes a rotatable tip release grip section 208, a port section 210, a stationary main grip section 212, and a rotatable driver grip section 214. Handle component 102 has a multiple part housing that is constructed of molded plastic pieces that primarily snap together to form the housing. An access housing part 218 having a left piece L and a right piece R that snap together along a longitudinally extending seam forms an external proximal portion 218A of the handle component housing and an internal distal portion 218B of the handle component housing that is disposed to extend within main grip section 212 and driver grip section 214, which will be described in more detail below. Sheath component 104 is an elongate tubular member defining a lumen from a proximal end to a distal end thereof that is sized, inter alia, to receive up to a 13 Fr or French medical device, which may be a catheter, such a branch stent-graft delivery system, or other interventional device having up to a 4.3 mm diameter, therethrough. In an embodiment, tubular sheath component 104 may be formed from a composite material having a braided layer of polyether block amide, such as PEBAX®, that is sandwiched between layers of polyamide 12, such as VESTAMID®.

Tip release grip section 208 of handle component 102 is a rotatable knob that may be turned by an operator to selectively actuate a tip capture mechanism 320 of distal tip assembly 106, which is shown best in FIG. 3A that depicts sheath component 104 proximally refracted from distal tip assembly 106. Tip release grip section 208 is attached to a proximal portion of an elongate tubular member 222, which defines a lumen therethrough that forms at least a portion of a main guidewire lumen of delivery system 100 that extends from a proximal end 101 to a distal end 103 of the delivery system, with a proximal port of the main guidewire lumen being at proximal end 101 and a distal port of the main guidewire lumen being at distal end 103. Rotation of tip release section 208 rotates tubular member 222 to thereby effectuate the distal movement of a sleeve 324 of tip capture mechanism 320 that is operably coupled to a distal end of tubular member 222. The distal movement of sleeve 324 exposes a spindle 326 of tip capture mechanism 320 to permit the release of a proximal anchoring stent of a main stent-graft, such as a proximal anchoring stent 1081 of a main stent-graft 1080 in FIG. 10. Additional detail and functionality of distal tip assembly 106 is described with reference to the embodiment of FIGS. 11, 11A, 11B and 12 of U.S. application Ser. No. 13/447,101 to Argentine, which was filed on Apr. 13, 2012 and is incorporated by reference herein in its entirety. A tip release safety lock 107, shown in a partial sectional view of delivery system 100 in FIG. 1B, prevents rotation of tip release grip section 208 until each of a middle member component 233 and a trigger wire pull tab 109, each of which will be discussed in greater detail below, are removed from delivery system 100 to thereby prevent out-of-sequence deployment of the proximal anchoring stent of the main stent-graft, such as proximal anchoring stent 1081 of main stent-graft 1080 shown in FIG. 10. Trigger wire pull tab 109 is a molded component that includes an inwardly extending catch 109' (shown more clearly in FIG. 12) that fits within a longitudinal opening 107' of tip release safety lock 107 to prevent rotation thereof.

Figure 2C:
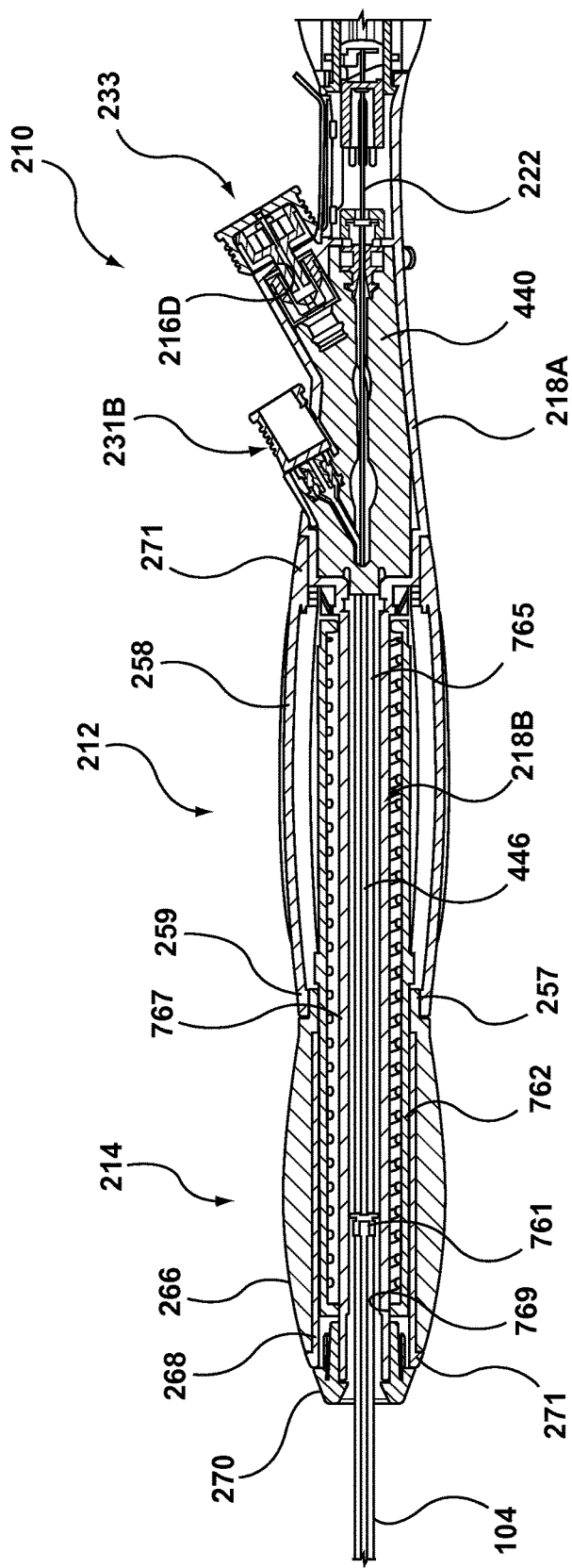
FIG. 2C is a sectional view of a portion of the handle component of the delivery system shown in FIG. 1 taken along line C-C.

With reference to FIGS. 2A-2C, port section 210 of handle component 102 includes a first branch guidewire access port 216A, a second branch guidewire access port 216B, a third branch guidewire access port 216C and a middle member access port 216D. Each access port 216A-216C forms an inlet/outlet of a respective removable lumen component 231A, 231B, 231C that is disposed within a molded opening formed in a main seal structure 440, as described in more detail below. Main seal structure 440 is disposed within external proximal portion 218A of access housing 218 and functions as a sealing manifold for the components of and those associated with the access ports of handle component 102. In contrast to access ports 216A-216C, middle member access port 216D is a tubular outlet formed in external proximal portion 218A of access housing 218 that is proximal of access ports 216A-216C and oriented at an acute angle relative to a longitudinal axis of delivery system 100. Second branch guidewire access port 216B is aligned along the delivery system longitudinal axis with middle member access port 216D and first and third branch guidewire access ports 216A, 216C are aligned with each other on opposing sides of the delivery system longitudinal axis and longitudinally disposed between second branch guidewire access port 216B and middle member access port 216D. Each of the branch guidewire access ports 216A, 216B, 216C is configured to receive a guidewire, as described in detail below, and is positioned on handle component 102 to anatomically correspond to a vessel, such as the right renal artery (RRA), superior mesenteric artery (SMA) and the left renal artery (LRA), respectively, to which each is intended to deliver the guidewire so as to make the device intuitive for use by an operator. Middle member access port 216D is configured to receive a removable middle member component 233 therethrough, as described in detail below.

Figure 4:
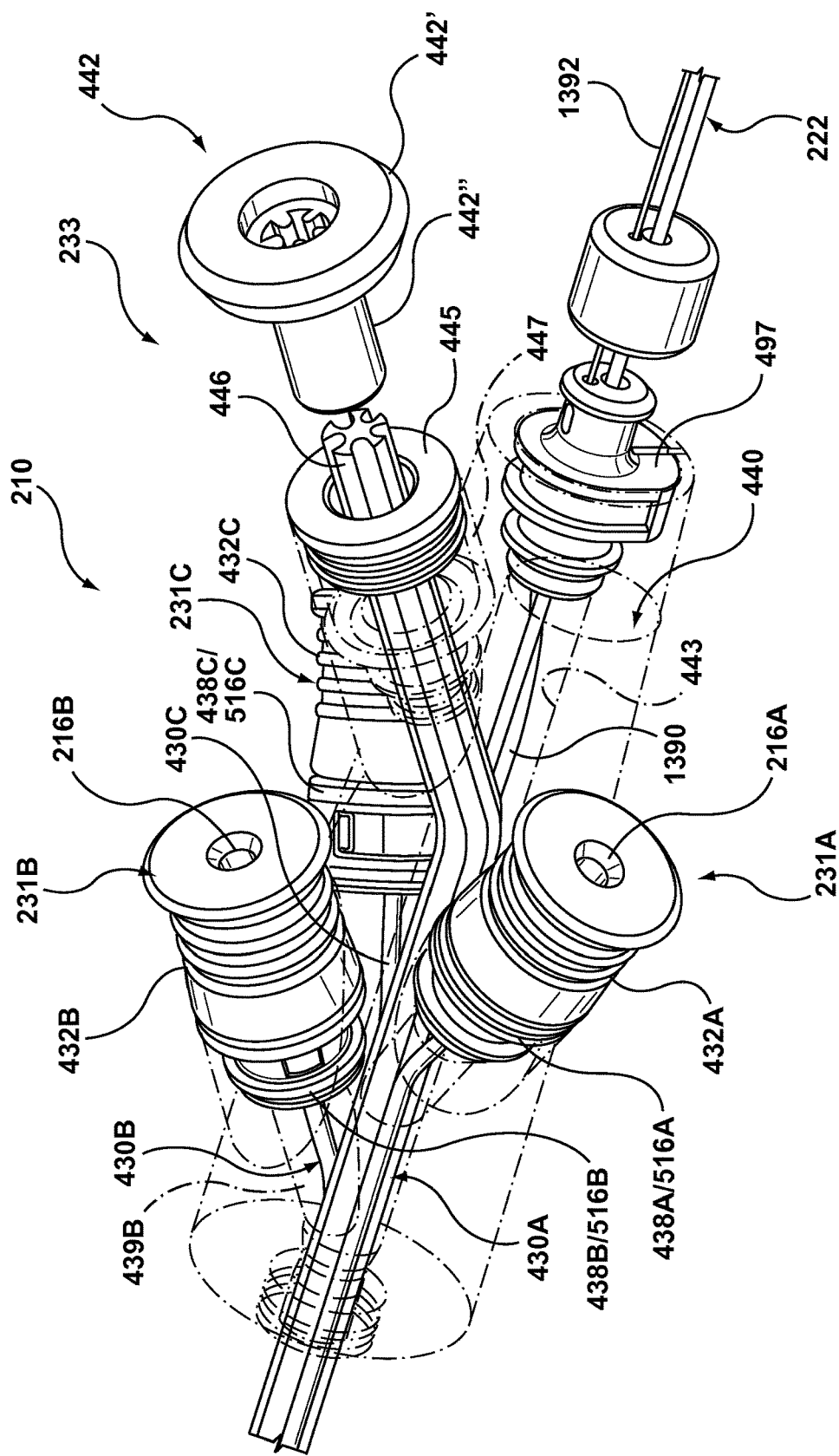
FIG. 4 is a perspective view of a port section of the handle component of the delivery system shown in FIG. 1 with an access housing component removed.

FIGS. 4 and 5 show the sealing structures that are contained within port section 210 to ensure hemostasis at the various access ports, with FIG. 4 being a perspective view of the internal structures within port section 210 with access housing 218 removed and FIG. 5 being a sectional view of port section 210 taken along line 5-5 of FIG. 2A. Each removable lumen component 231A, 231B, 231C includes an elongated guidewire tube 430A, 430B, 430C (distal ends of which may be seen in FIG. 3A) with a respective access port seal component 432A, 432B, 432C attached at a proximal end thereof. In embodiments hereof, guidewire tubes 430A, 430B, 430C may a polymeric tubing of polyamide 12, such as VESTAMID®.

Access port seal component 432B of removable lumen component 231B is described with reference to FIG. 5 and is representative of the structures and functions of access port seal components 432A, 432C of removable lumen component 231A, 231C. Access port seal component 432B includes a seal portion 434B with access port 216B therethrough and a coupling portion 436B for removably coupling lumen component 231B to a hemostasis seal 438B held within main seal structure 440. Access port seal component 432B may be considered an external seal component defining an outer access port 216B therethrough and hemostasis seal 438B may be considered an internal seal component defining an inner access port 516B therethrough, wherein the external seal component 432B and the internal seal component 438B together form a reconfigurable porting structure.

In embodiments hereof, coupling portion 436B of access port seal component 432B may be a molded component formed from acrylonitrile butadiene styrene (ABS) or an equivalent material thereto, and seal portion 434B, hemostasis seal 438B and main seal structure 440 may be molded components formed from silicone or another material suitable for providing a seal with the access port structures held therein or defined thereby and/or for providing a seal for various medical devices, for e.g., guidewires, balloon catheters and/or branch delivery catheters, that are deployed therethrough. In an embodiment, coupling portion 436B and hemostasis seal 438B have a reversible snap-fit. In another embodiment, coupling portion 436B slides within inner access port 516B of hemostasis seal 438B to have a frictional or interference fit therewith. Coupling portion 436B has a bore that extends therethrough that is sized to receive the proximal end of guidewire tube 430B. Guidewire tube 430B extends through a distal opening 438B' of hemostasis seal 438B such that hemostasis seal 438B maintains a sealing surface there around.

Access port 216B of access port or external seal component 432B permits the introduction of a guidewire (not shown) into a lumen 437 of guidewire tube 430B. As discussed in detail below, after a guidewire is introduced through guidewire tube 430B, removable lumen component 231B is removed from delivery system 100 and delivery system 100 is otherwise reconfigured to its delivery sheath configuration, hemostasis seal or internal seal component 438B defines an inner access port 516B, which may also be considered a delivery sheath port 516B, to permit the introduction of medical devices over the guidewire that extends therethrough. It should be understood from this description that hemostasis seal or inner seal component 438B defining inner access port 516B upon the removal of access port or external seal component 432B is representative of the structures and functions of hemostasis seals or inner seal components 438A, 438C, which define respective inner access ports 516A, 516C upon the removal of access port or external seal components 432A, 432C, respectively, therefrom.

Access port 216B is a small molded hole within seal portion 434B that leads to a narrow passageway 435' of a guidewire passageway 435 of access port seal component 432B. A diameter of the molded hole that forms access port 216B is sized to be substantially equal to or slightly less than a diameter of a guidewire that is to be introduced therethrough in order to maintain hemostasis therebetween. In an embodiment, the molded hole that forms access port 216B may have a diameter of between 0.010 inch and 0.035 inch. In order to insert a guidewire (not shown) through access port 216B of seal portion 434B, a reduced-diameter male portion 551 of an access port or seal dilator 550 is first engaged with access port 216B to dilate the molded hole that forms access port 216, as shown in FIGS. 5 and 5A. In an embodiment, access port dilator male portion 551 includes a radially-extending ring 554 in an outer surface thereof that mates with a corresponding groove within access port 216B. Access port dilator 550 defines a lumen 552 through which the guidewire is tracked to be inserted through narrow passageway 435' of seal portion 434B. Once the guidewire is positioned to extend through passageway 435 and within at least a portion of guidewire tube lumen 437, seal dilator 550 is removed so that the diameter of access port 216B returns to its original diameter to thereby provide a hemostatic seal over the guidewire. Access port dilator lumen 552 has a tapered diameter that readily accepts a floppy ended guidewire while providing column strength thereto to facilitate easier introduction. The use of access port dilator 550 also provides the benefit of access port 216B being a smaller diameter hole than would otherwise be required to permit the passage of a guidewire therethrough. Additionally, access port dilator 550 includes a flange 553 that is configured to be fluidly coupled to a source of fluid to enable it to be used as a flushing tool for access port seal components 432A, 432B, 432C.

Middle member component 233 is shown removed from delivery system 100 in FIG. 6 with an enlarged view of a distal portion 655 of middle member component 233 being depicted in FIG. 6A. With reference to FIGS. 4 and 5, middle member component 233 includes a middle member handle 442 that is a molded component defining a bore 441 therethrough for receiving a proximal end 449 of a middle member shaft 446. Middle member handle 442 has a proximal head 442', which radially extends from a distal tube segment 442", on which a middle member grip 444 is secured for being gripped by an operator. In an embodiment, middle member grip may be a molded component formed from silicone. Middle member component 233 is removably coupled to delivery system 100 via access port 216D, which has a hemostasis seal 445 held therein by a seal housing 447, wherein hemostasis seal 445 functions very much like a duckbill valve to completely close when the middle member component is removed therefrom. In embodiments hereof, seal housing 447 may be a molded component formed from acrylonitrile butadiene styrene (ABS) or an equivalent material thereto, and hemostasis seal 445 may be a molded component formed from silicone or another material suitable for providing a seal with the middle member component inserted therethrough. More particularly, seal housing 447 has a distal surface that abuts against main seal structure 440 to substantially wedge hemostasis seal 445 against an interior surface of a rim of access port 216D. When middle member component 233 is fully inserted within access port 216D to be removably coupled therewith, proximal head 442' of middle member handle 442 sits against an exterior surface of the rim of access port 216D, distal tube segment 442" of middle member handle 442 is inserted within and sealed around by hemostasis seal 445 and middle member shaft 446 extends through a central bore 443 of main seal structure 440, as well as the remainder of handle component 102, such that a distal end 448 of middle member shaft 446 extends proximal of a stent-graft delivery area 321 defined within a distal portion of sheath component 104, as will be discussed in more detail below.

With reference to FIGS. 5 and 6, middle member shaft 446 has a bend that angles proximal end 449 thereof away from the longitudinal axis of delivery system 100 with the middle member shaft portion disposed proximal of the bend being of a length to extend between access port 216D and central bore 443 of main seal structure 440 when middle member component 233 is installed within delivery system 100. In an embodiment, proximal end 449 of middle member shaft 446 is at an angle of 30° relative to the longitudinal axis of the delivery system.

With reference to FIGS. 1A, 3A and 6A, middle member shaft 446 has five external grooves 656A, 656B, 656C, 656D, 656E formed within an exterior surface thereof, each of which extends from proximal end 449 to distal end 448 of middle member shaft 446. Middle member shaft 446 may be described as having a star-shaped cross-section due to the symmetrical placement of the grooves about the perimeter of the shaft. In an embodiment, middle member shaft 446 is an extruded shaft of polyethylene or a polyether block amide, such as PEBAX®. Each groove 656A, 656B, 656C, 656D, 656E of middle member shaft 446 is sized to permit passage therethrough of any one of elongate tubular member 222, elongate guidewire tubes 430A, 430B, 430C and a distal stent-graft capture tube 1390 that contains a trigger wire 1392, which will be discussed below with reference to FIGS. 13 and 13A. In an embodiment, grooves 656A, 656B, 656C, 656D, 656E are substantially U-shaped channels having a width W to accommodate a diameter of the tube or tubular member that they house, and a depth D that is substantially equal to the width W thereof. Accordingly in embodiments hereof, each groove 656A, 656B, 656C, 656D, 656E may have the same width and depth or a different width and depth as one or more of the other grooves depending on the diameter of the tube or tubular member that is intended to be used therewith. In an embodiment hereof, grooves 656A, 656B, 656E may have a width and depth of 0.072 inch to accommodate elongate guidewire tubes 430A, 430B, 430C, respectively, and grooves 656C, 656E may have a width and depth of 0.056 inch to accommodate elongate tubular member 222 and distal stent-graft capture tube 1390, respectively.

As noted above, middle member shaft 446 extends through port section 210, main grip section 212, and driver grip section 214 of handle component 102 such that a distal portion of middle member shaft 446 resides within a sheath lumen 105 defined by tubular sheath component 104. Each of elongate tubular member 222, elongate guidewire tubes 430A, 430B, 430C and distal graft capture tube 1390 is introduced into a respective groove 656A, 656B, 656C, 656D, 656E of middle member shaft 446 within central bore 443 of main seal structure 443, as best shown in FIG. 5. For example when removable lumen component 231B is to be engaged with delivery system 100, a distal end of guidewire tube 430B is inserted through hemostasis valve 438B to be tracked through an entry channel 439B of main seal structure 440 into groove 656A of middle member shaft 446 that extends within main seal structure central bore 443 such that continued advancement of guidewire tube 430B slides the tube within groove 656A until access port seal component 432B mates within hemostasis seal 438B. In an embodiment, the middle member component may be rotated in order to adjust for any misalignment that may occur between a groove and its respective entry channel when the middle member component is inserted within its access port. Similarly, each of guidewire tubes 430A, 430C of removable lumen components 231A, 231C is also introduced into respective grooves 656B, 656E on opposing sides of middle member shaft 446 through its respective hemostasis seal and main seal structure entry channel and tracked through its respective groove 656B, 656E until its access port seal component 432A, 432C is seated within its respective hemostasis seal.

Figure 10:
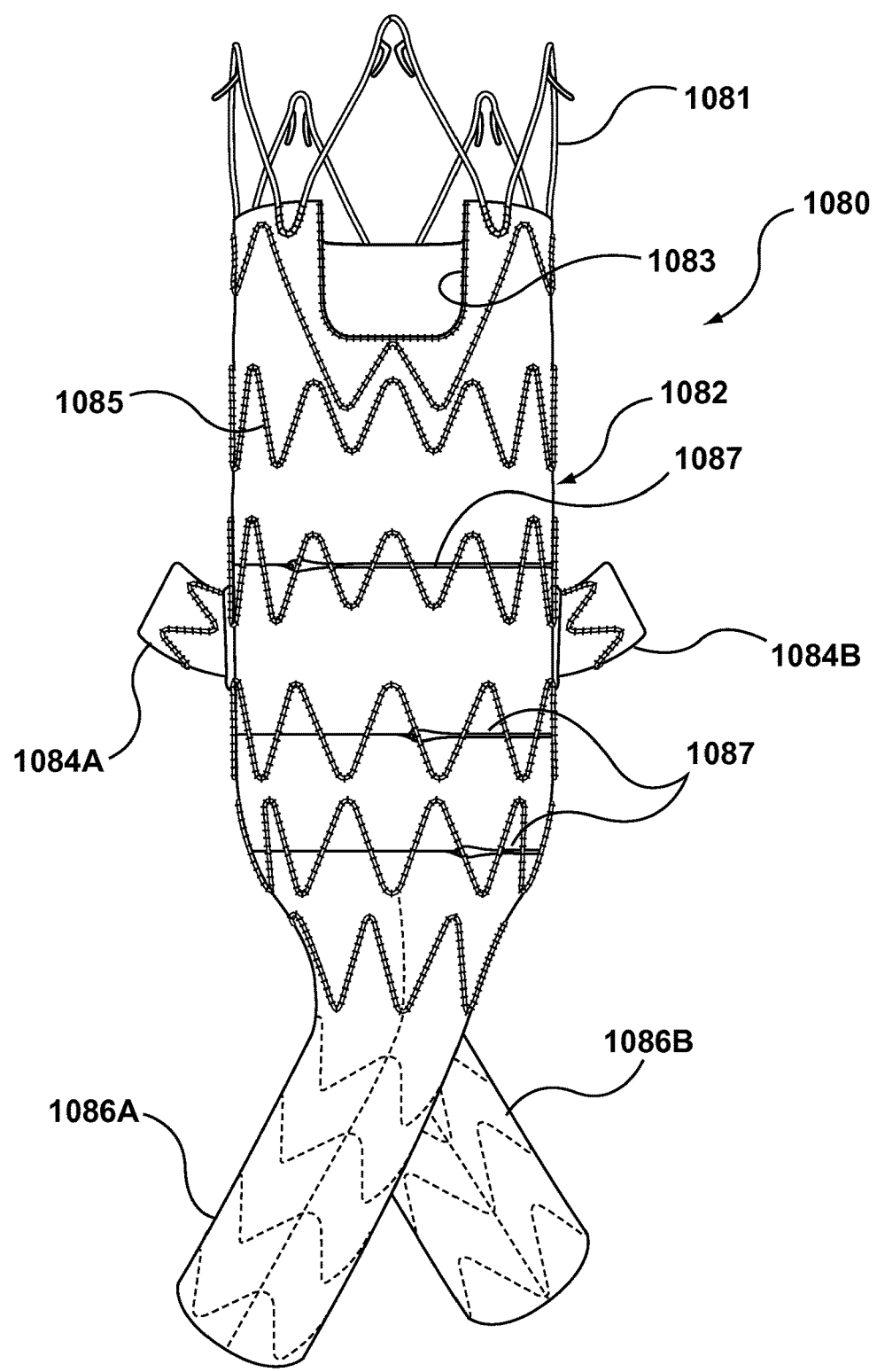
FIG. 10 depicts a main stent-graft that may be delivered by the delivery system of FIG. 1.

With middle member shaft 446 inserted within sheath component104, sheath lumen 105 is effectively divided into five working lumens due to grooves 656A, 656B, 656C, 656D, 656E of middle member shaft 446 so that delivery system 100 is configured in a multi-lumen delivery catheter configuration to deliver a self-expanding main stent-graft, such as main stent-graft 1080 shown in FIG. 10, to a treatment site. Conversely, the removal of middle member component 233 re-configures delivery system 100 to a single lumen delivery sheath configuration, such that sheath component lumen 105 is no longer divided into five working lumens, and thereafter functions as a delivery sheath for use with guidewires, guide catheters, and the like, and/or branch delivery system(s), such as branch delivery catheters 2396A, 2396B shown in FIGS. 23-25, that are used to introduce and deploy branch stent-graft(s), such as branch stent-grafts 2698A, 2698B shown in FIGS. 26 and 27, between the main stent-graft and a respective branch vessel(s).

FIGS. 7, 8 and 8A are views of a portion of delivery system 100 that show main grip section 212 and driver grip section 214 of handle component 102 partially disassembled. External proximal portion 218A and internal distal portion 218B of access housing part 218 are shown in FIG. 7 and are removed in FIG. 8, such that main seal housing 440 of port section 210 as well as various components of main grip and driver grip sections 212, 214 that permit the proximal retraction, or longitudinal translation, of sheath component 104 may be more clearly seen in FIG. 8. In order to reduce a length of handle component 102 so that delivery system 100 is compatible for use as a delivery sheath for standard 100 cm medical devices, embodiments hereof incorporate a screw gear assembly 760 having an internally-oriented thread pattern with concentric main grip and driver grip sections 212, 214 radially disposed thereover to be concentric therewith. Such a sheath transmission arrangement for retracting the portion of sheath component 104 that covers stent-graft delivery area 321 to deploy or release a main stent-graft compressed therein beneficially provides a shorter length for handle component 102 enabling compatibility with off-the-shelf catheters.

Screw gear assembly 760 includes a tubular screw gear clamshell component 762 having first and second halves 762A, 762B that join together along mating longitudinally extending surfaces to enclose, inter alia, a driver screw nut 761 and internal distal portion 218B of access housing part 218. In an embodiment, first and second halves 762A, 762B of screw gear clamshell component 762 are snap-fit together. Screw gear clamshell component 762 includes internally-oriented threads 763 that are discontinuous between first and second halves 762A, 762B such that a first set of threads 763A are formed to internally extend from an inner surface of clamshell component first half 762A toward the longitudinal axis of delivery system 100 and a second set of threads 763B are formed to internally extend from an inner surface of clamshell component second half 762B toward the longitudinal axis of delivery system 100. The discontinuous internal thread pattern is beneficial in that it is not a full thread thereby reducing the undercuts that must normally be made with internally-oriented threads and providing relative ease of manufacture. In contrast, driver screw nut 761 has an externally-oriented corresponding thread 764 that extends around the entire circumference of screw nut 761, i.e., one complete revolution, to maintain smooth functionality, i.e., smooth longitudinal translation of the sheath component. When screw gear clamshell component 762 is rotated by driver grip section 214 of handle component 102 in a first direction, external thread 764 of driver screw nut 761 mates with internal threads 763A, 763B of clamshell halves 762A, 762B to proximally retract tubular sheath component 104, which is coupled to driver screw nut 761, toward an operator to uncover stent-graft delivery area 321 to deploy or release a main stent-graft compressed therein. When screw gear clamshell component 762 is rotated in a second direction opposite of the first direction, external thread 764 of driver screw nut 761 mates with internal threads 763A, 763B of clamshell halves 762A, 762B to distally advance tubular sheath component 104 toward tip assembly 106.

Figure 2D:
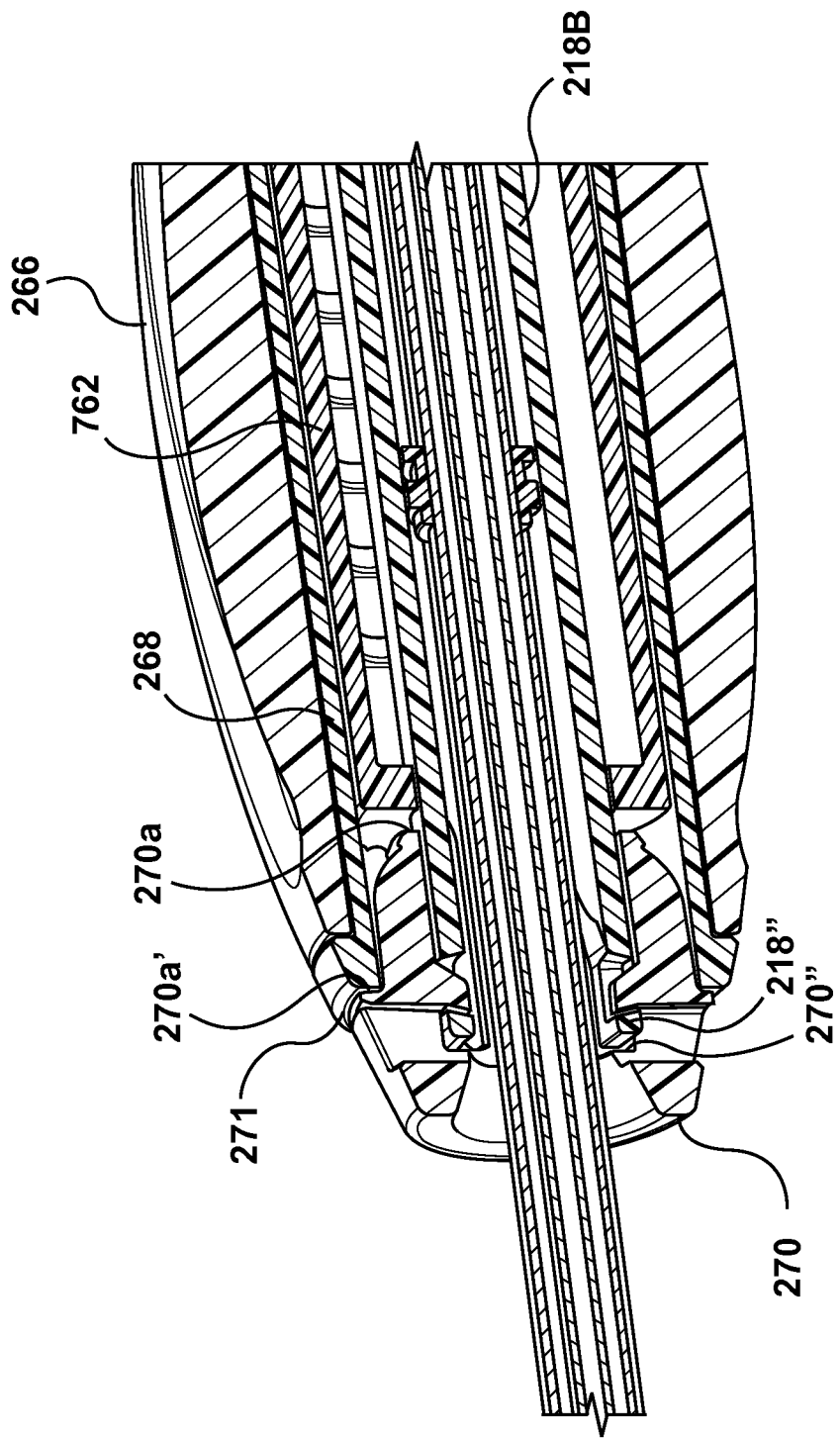
FIG. 2D is an enlarged sectional view of a distal end of the portion of the handle component shown in FIG. 2C.
Figure 8B:
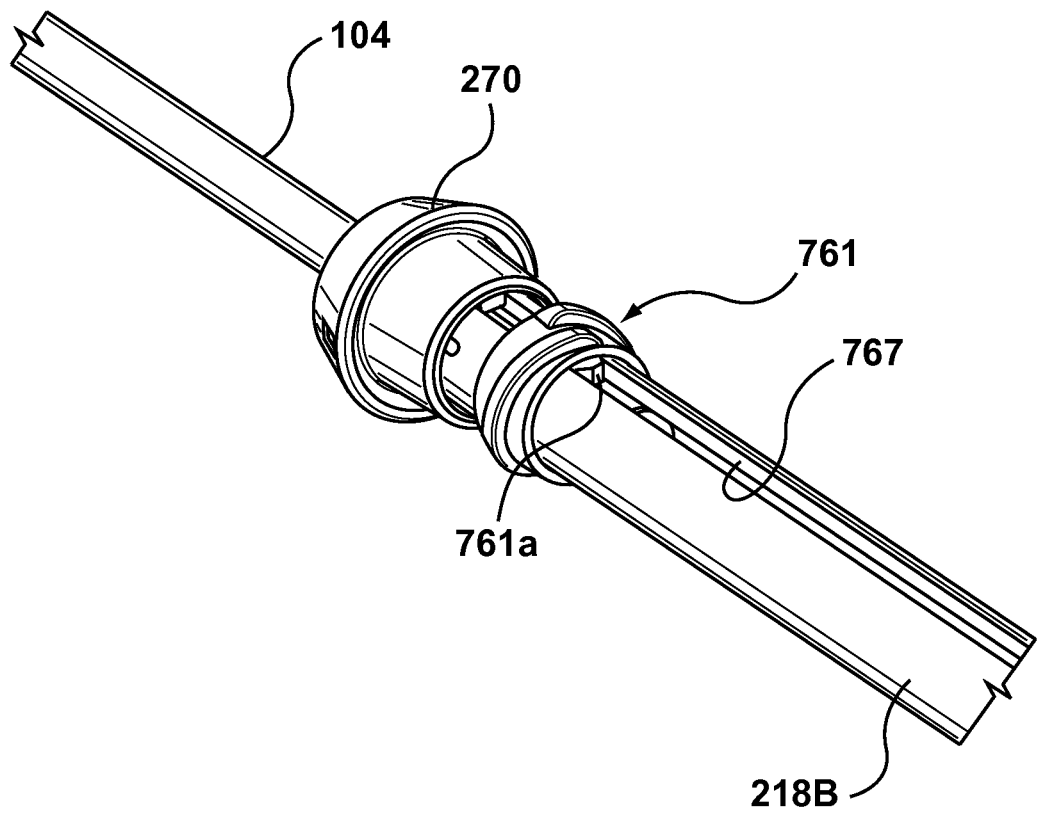

In order to longitudinally translate, such as to move proximally, driver screw nut 761 includes a hub 761' that is slidably disposed on a longitudinally-extending tubular shaft 765 within access housing distal portion 218B and a keyed opening, as best represented in FIG. 8B, that permits the thread portion 761" of driver screw nut 761 to slide over access housing distal portion 218B with an inwardly extending key 761a of driver screw nut 761 sliding within a slot 767 in distal portion 218B to prevent unwanted rotation of driver screw nut 761. With reference to FIG. 2C, middle member shaft 446 is slidably disposed within tubular shaft 765 as it extends through main grip section 212 and driver grip section 214 of handle component 102. Screw gear clamshell component 763 has a bearing surface 769 on each of its proximal and distal ends that bear against access housing distal portion 218B during rotation thereof. Screw gear clamshell 762 is held in its longitudinal position relative to the remainder of handle component 102 by being trapped between access housing proximal portion 218A and proximal end surfaces 270a, 270a' of a strain relief nut 270, as best shown in FIG. 2D. With reference to FIG. 2C, driver grip section 214 of handle component 102 includes a driver grip cover 266 that is attached to a gear driver cylinder 268 that in turn is attached to screw gear clamshell component 762 to effectuate the rotation thereof. Driver grip cover 266, gear driver cylinder 268 and clamshell component 762 are operably coupled and longitudinally held together relative to each other to be rotated in unison. Gear driver cylinder 268 has a distal end 271 that snaps onto strain relief nut 270 to be rotatable relative thereto whereas driver grip cover 266 has a proximal end 257 that snaps together with a distal end 259 of a main grip cover 258 to be rotatable relative thereto. The friction interface between driver grip cover proximal end 257 and main grip cover distal end 259 adds some frictional resistance for control of rotation. Without this resistance, there is a risk of pre-mature retraction of sheath component 104 from covering the main stent-graft held in a delivery configuration therein. Conversely, a proximal end 271 of main grip cover 258 is snapped over a proximal end of access housing distal portion 218B in a non-rotatable fashion so as to be stationary during use.

Figure 9:
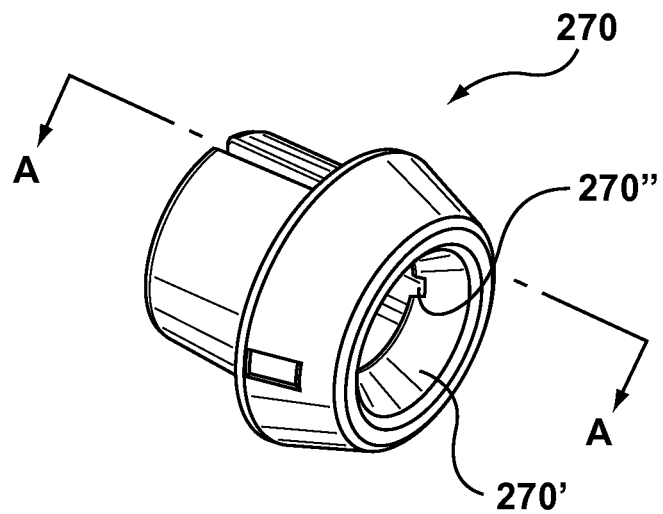
FIG. 9 is a perspective view of a strain relief nut removed from the delivery system shown in FIG. 1 with FIG. 9A being a sectional view thereof taken along A-A in FIG. 9.
Figure 9A:
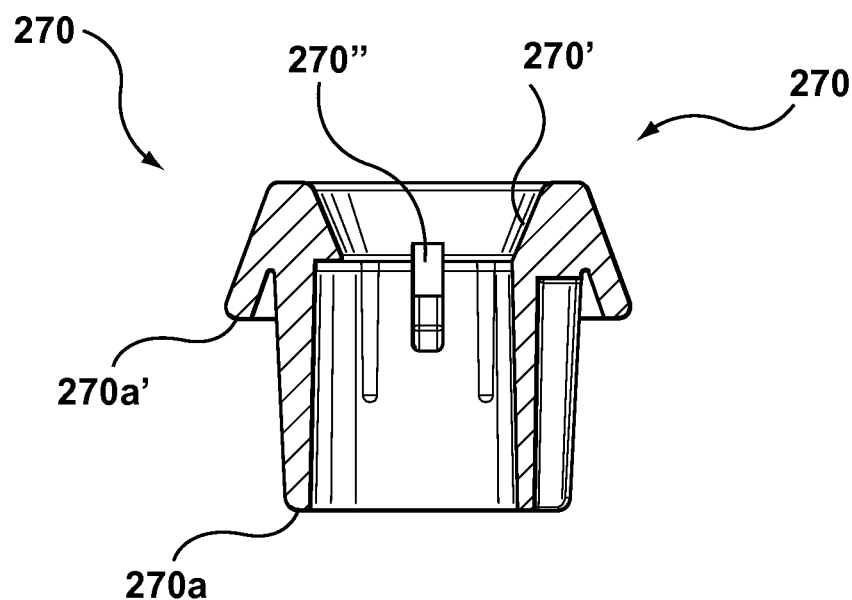

FIG. 9 is a perspective view of strain relief nut 270 removed from delivery system 100 with FIG. 9A being a sectional view thereof taken along A-A in FIG. 9. Strain relief nut 270 includes an internally constraining design with a flared distal opening 270' that permits sheath component 104 to bend gradually as it exits handle component 102. Strain relief nut 270 constrains a profile of the inside bend radii where sheath component 104 enters delivery system 100 via the inside geometry of the strain relief nut 270 permitting a shorter overall length for handle component 102, so that delivery system 100 is compatible for use as a delivery sheath for standard 100 cm medical devices. Strain relief nut 270 also acts as a retaining nut for holding the various components of handle component 102 together. In order to perform the function of a retaining nut, strain relief nut 270 includes a socket 270" into which snaps or sits a corresponding protrusion 218" at a distal end of access housing distal portion 218B such that proximal end surfaces 270a, 270a' of a strain relief nut 270 bear against distal end surfaces of access housing distal portion 218B and gear driver cylinder 268, respectively, to hold the structures of main grip section 212 and driver grip section 214 against access housing proximal portion 218A.

FIG. 10 depicts a main stent-graft 1080 for delivery within the aorta by delivery system 100, although it should be apparent to one of ordinary skill in the art after that delivery system 100 may be used for delivering other stent-graft designs that do not include all the features of main stent-graft 1080 and which may be deployed within a vessel other than the aorta. Main stent-graft 1080 is described in detail in U.S. application Ser. Nos. [13/458,209 and 13/458,242] to Coghlan et al., each of which was filed on a date concurrent herewith and is incorporated by reference herein in its entirety, and therefore only certain features will be described herein to illustrate the use of delivery system 100 therewith.

Main stent-graft 1080 is shown in its expanded configuration in FIG. 10 substantially how it would look deployed within a main vessel, such as the aorta. Main stent-graft 1080 includes a proximal self-expanding anchor stent 1081, a tubular graft body 1082 with a vessel lumen cut-out 1083 along a proximal end thereof, first and second branch graft couplings 1084A, 1084B extending from a midsection thereof, and first and second legs 1086A, 1086B distally extending from a bifurcation of tubular graft body 1082 to be positioned posterior and anterior of each other when main stent-graft is deployed within the aorta. As described in more detail below, first and second branch graft couplings 1084A, 1084B are configured to receive first and second branch stent-grafts 2698A, 2698B that are to be disposed between main stent-graft 1080 and corresponding branch vessels, such as the left and right renal arteries, and first and second legs 1086A, 1086B are configured to receive first and second limb stent-grafts 2799A, 2799B that are to be disposed between main stent-graft 1080 and corresponding downstream vessels that bifurcate therefrom, such as the left and right common iliac arteries that bifurcate from the abdominal aorta. Tubular graft body 1082 has a plurality of self-expanding stents, for example stent 1085, attached thereto that serve various functions, such as anchoring, sealing and coupling as explained in detail in U.S. application Ser. Nos. [13/458,209 and 13/458,242] to Coghlan et al., which were incorporated by reference above, and will not be explained in further detail herein. In embodiments hereof, tubular graft body 1082 may be formed from any suitable graft material, for example and not limited to, a low-porosity woven or knit polyester, DACRON material, expanded polytetrafluoroethylene, polyurethane, silicone, ultra high molecular weight polyethylene, or other suitable materials.

Figure 11:
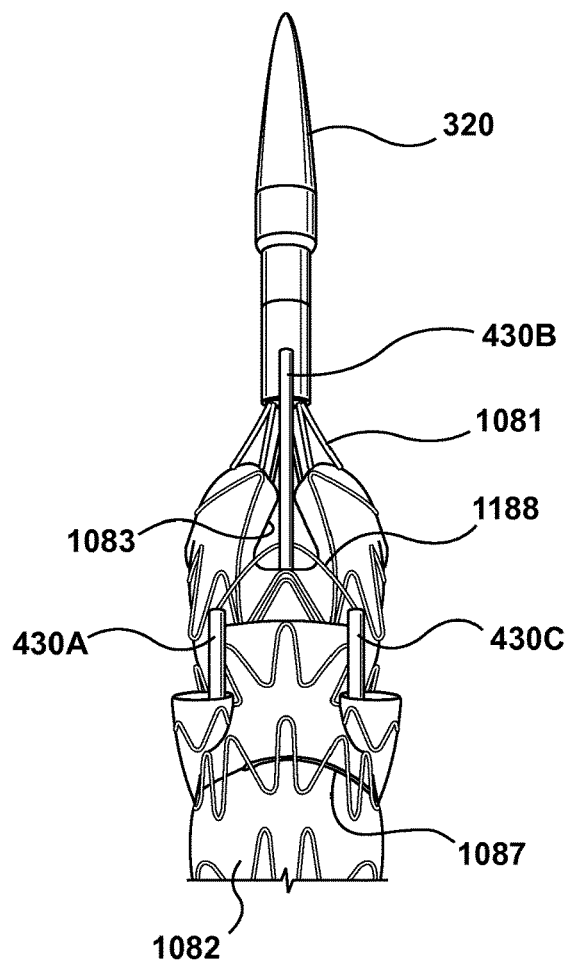
FIG. 11 depicts a proximal end of the main stent-graft of FIG. 11 in a partially expanded/compressed configuration attached to the delivery system of FIG. 1.

With reference to FIGS. 3, 3A and 11, main stent-graft 1080 is loaded and compressed into a delivery configuration within stent-graft delivery area 321 by sheath component 104 by first positioning main stent graft 1080 over such stent graft delivery area 321 so that distal ends of guidewire tubes 430A, 430C are respectively positioned to distally extend from first and second branch graft couplings 1084A, 1084B and so that the distal end of guidewire tube 430B is positioned to extend from vessel lumen cut-out 1083. With reference to FIG. 11, proximal crowns of proximal anchor stent 1081 are then secured by tip capture mechanism 320 so as to compress the proximal end of main stent-graft 1080. Main stent graft 1080 also includes circumferentially constraining sutures 1087 (shown in their preloaded state in FIG. 10), which may be of any suitable suture material, that are tightened around graft body 1082 to compress the self-expanding stents attached thereto to a smaller diameter for facilitating the loading of main stent-graft 1080 within lumen 105 of sheath component 104 and to allow space for various catheter tip shapes above branch graft couplings 1084A, 1084B during cannulation of the renal arteries during the procedure. The function and structure of circumferentially constraining sutures 1087 are discussed in detail in U.S. application Ser. No. [13/458,076] to Pearson et al., which was filed on a date concurrent herewith and is incorporated by reference herein in its entirety, and therefore only certain features will be described herein to illustrate the use of delivery system 100 therewith.

Figure 12:
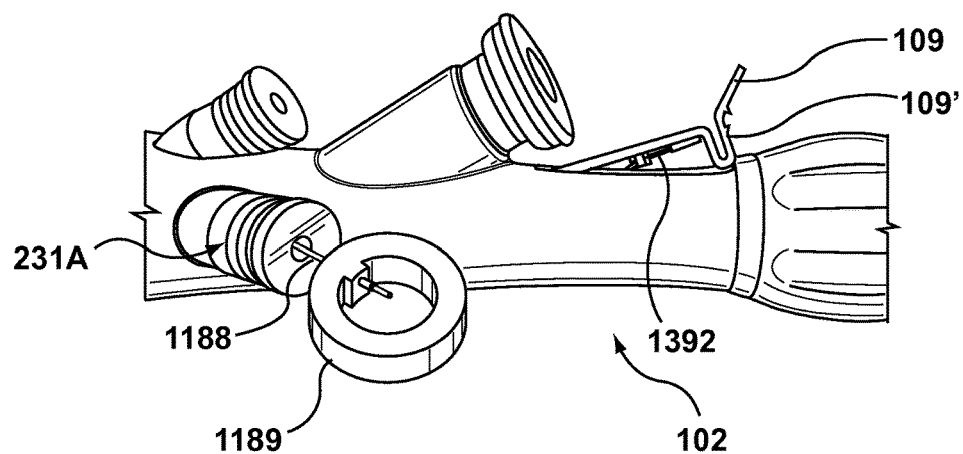
FIG. 12 is an enlarged alternate view of a portion of the handle component of FIG. 1.

A removable lifting wire 1188 is used to lift the distal end of guidewire tube 430B out of or external of the opening of vessel lumen cut-out 1083 to provide better control of the location of the distal end of guidewire tube 430B during deployment of main stent graft 1080. In this manner, lifting wire 1188 lifts the distal end of guidewire tube 430B external or outward of main stent-graft 1080, when the main-stent-graft is compressed in its delivery configuration within sheath component 104 of delivery system 100 as well as when main stent-graft 1080 is partially released therefrom, as shown in FIG. 11. In an embodiment, lifting wire 1188 may be of nitinol. Lifting wire 1188 is routed through guidewire tube 430A crossed under or inward of guidewire tube 430B within vessel lumen cut-out 1083 and then routed into guidewire tube 430C in which it terminates. In an embodiment, lifting wire 1188 may also be routed through capture points in the graft material on either side of vessel lumen cut-out 1083 to ensure that lifting wire 1188 stays anchored in such a position as to ensure guidewire tube 430B is supported by the lifting wire and to accurately locate a longitudinal position of lifting wire 1188. As shown in FIG. 12, a proximal end of lifting wire 1188 is attached to a pull ring 1189 that is accessible to an operator at access port seal component 432A when removal of wire 1188 is desired. The use of lifting wire 1118 to lift guidewire tube 430B ensures correct placement of a guidewire that is to be used therethrough to cannulate a branch vessel off of a main vessel, such as the superior mesenteric artery (SMA) that branches from the abdominal aorta, without additional intervention to beneficially shorten procedure time.

Figure 13:
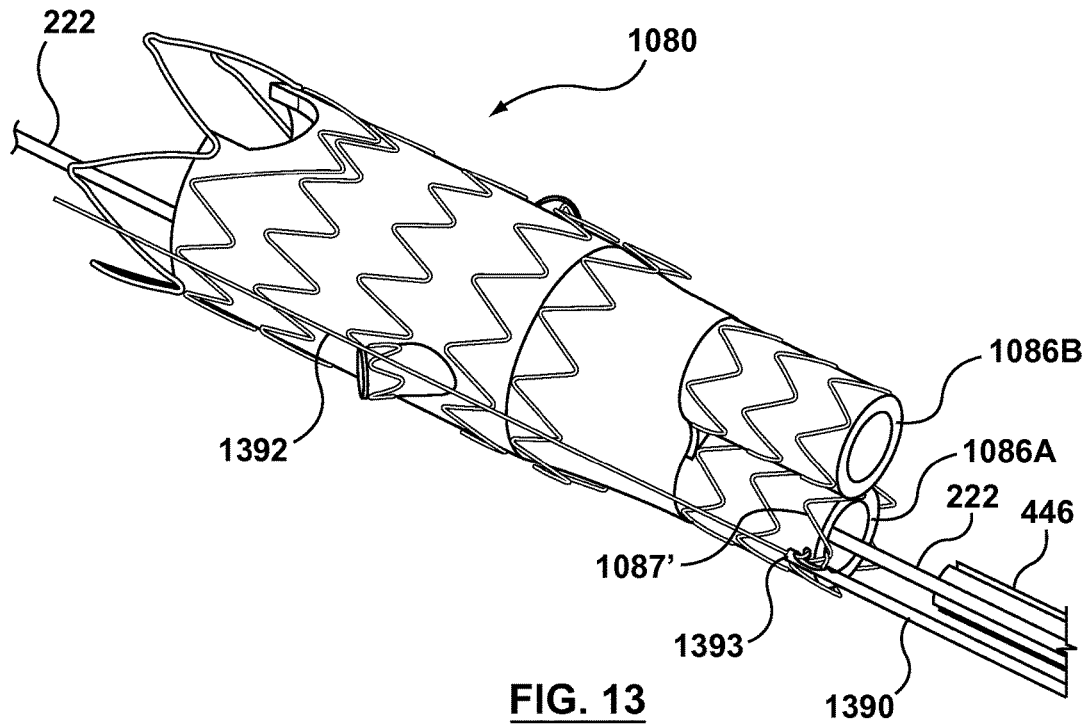
FIGS. 13 and 13A depict a distal stent-graft capture mechanism in accordance with an embodiment hereof.
Figure 13A:
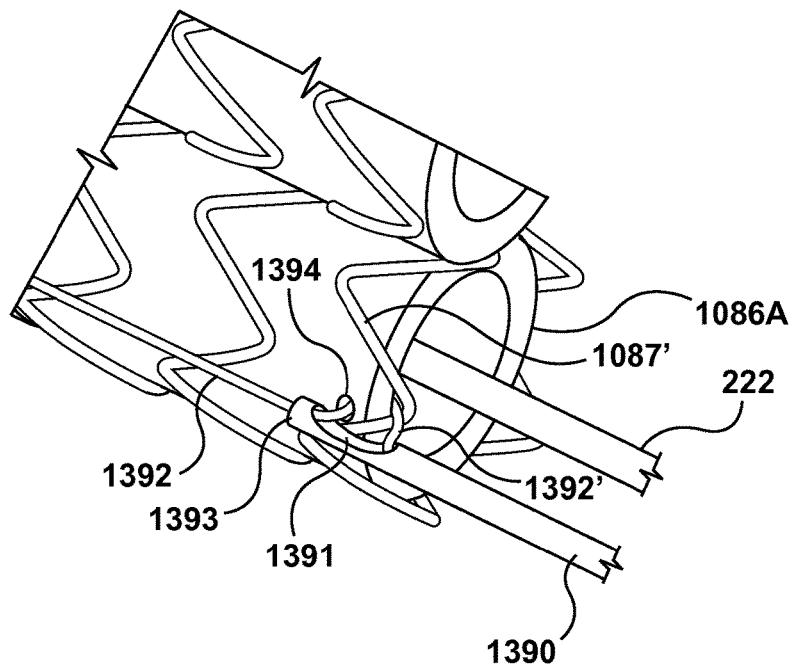

FIGS. 13 and 13A depict a distal stent-graft capture tube 1390 in accordance with an embodiment hereof that in conjunction with a circumferentially constraining suture trigger wire 1392, which is slidably disposed within a lumen thereof, captures or holds a distal end of main stent-graft 1080 and allows for its release when trigger wire 1392 is pulled out of handle component 102 by trigger wire pull tab 109. The lumen of distal stent-graft capture tube 1390 is defined thereby from a proximal port, which is attached to an anchor component 497 shown in FIG. 4, to a distal port 1393 thereof. Distal stent-graft capture tube 1390 includes a skived side surface that forms a half-moon shaped opening 1391 through a side wall thereof that is proximally spaced from distal port 1393. In an embodiment, half-moon shaped opening 1391 may be sized to allow a portion of an exposed distalmost stent of a main stent-graft to be slipped therein to be captured by trigger wire 1392. In the embodiment shown in FIGS. 13 and 13A, trigger wire 1392 is threaded out of opening 1391 to cross behind/under distalmost stent 1087' and through a hole 1394 in the graft material of main stent-graft leg 1086A to re-enter opening 1391 and then exit distal stent-graft capture tube 1390 via distal port 1393 thereby forming a loop 1392' with capture tube 1390 that extends from opening 1391. Thereafter trigger wire 1392 distally extends through the circumferentially constraining sutures to serve its primary function. In this manner, distal stent-graft capture tube 1390 and trigger wire 1392 form a distal stent-graft capture mechanism that is releasably attached to leg 1086A. Moreover the use of distal stent-graft capture tube 1390 and trigger wire 1392 in this manner allows a force to be applied to the distal section of main stent-graft 1080 to resist cranial migration thereof and to hold leg 1086A in place relative to the remainder of delivery system 100 during the introduction and deployment of the various medical devices that will be introduced therethrough, when delivery system 100 is re-configured for use as a delivery sheath during a remainder of the interventional procedure. It should be understood by this description that the distal stent-graft capture system depicted attached to leg 1086A in FIGS. 13 and 13A would be used with leg 1086B, if delivery system 100 had instead been inserted through leg 1086B during the loading of main stent-graft thereon.

Delivery system 100 in a multi-lumen delivery catheter configuration permits the delivery and staged release of main stent-graft 1080 and in a delivery sheath configuration permits the introduction of various medical devices for the delivery of various branch grafts, with the limb grafts that complete the stent-graft implant being introduced and deployed after delivery system 100 is removed from the aorta. FIGS. 14-27 depict a method of using delivery system 100 for treatment of a short-neck infrarenal abdominal aortic aneurysm AAA. An infrarenal AAA is located below the renal arteries, with RRA denoting the right renal artery and LRA denoting the left renal artery in FIGS. 14-27. In other methods in accordance with embodiments hereof, delivery system 100 may be used treat a juxtarenal AAA, which approaches or extends up to, but does not involve, the renal arteries, and a suprarenal AAA, which involves and extends above the renal arteries.

Figure 14:
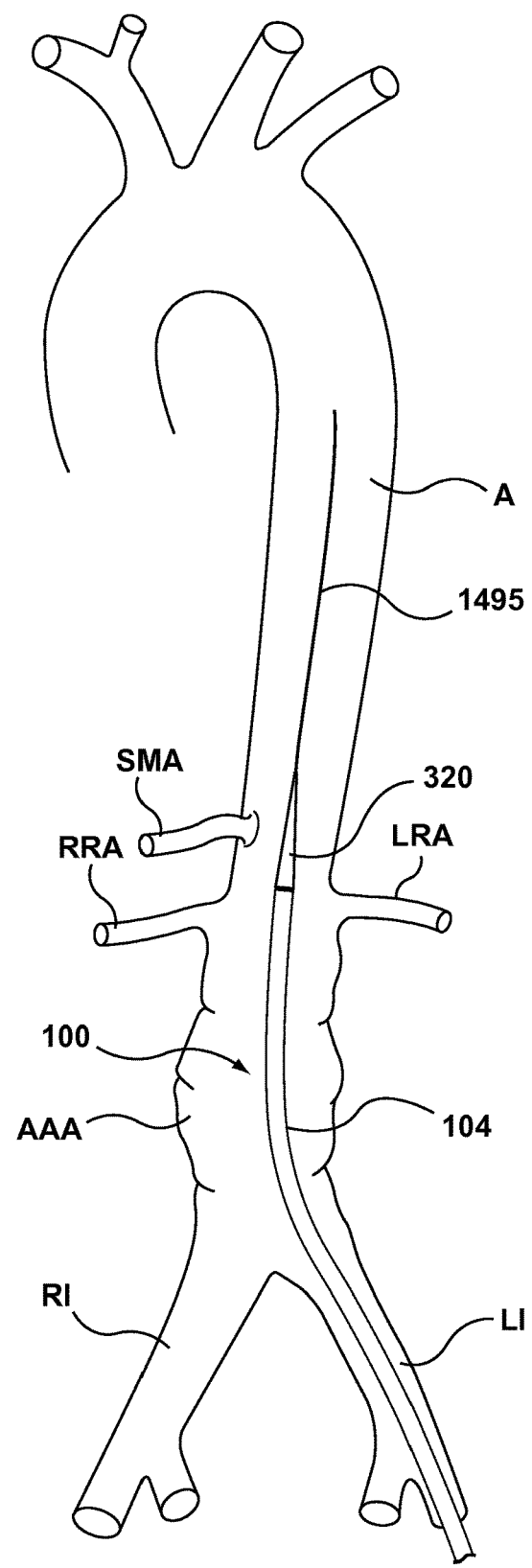
FIGS. 14-27 depict a method of using the delivery system of FIG. 1 for treatment of a short-neck infrarenal aneurysm.

FIG. 14 depicts delivery system 100 with main stent-graft 1080 loaded within sheath component 104 thereof (as described above) after the delivery system 100 has been tracked into the aorta A to a treatment site of the AAA such that tip capture mechanism 320 is positioned proximate the SMA. Delivery system 100 is shown tracked over a main guidewire 1495 that was previously positioned by being percutaneously introduced into a femoral artery and tracked therefrom through the left iliac artery LI to the abdominal aorta, as would be understood by one of ordinary skill in the art. Guidewire 1495 extends through elongate tubular member 222 of delivery system 100.

Figure 15:
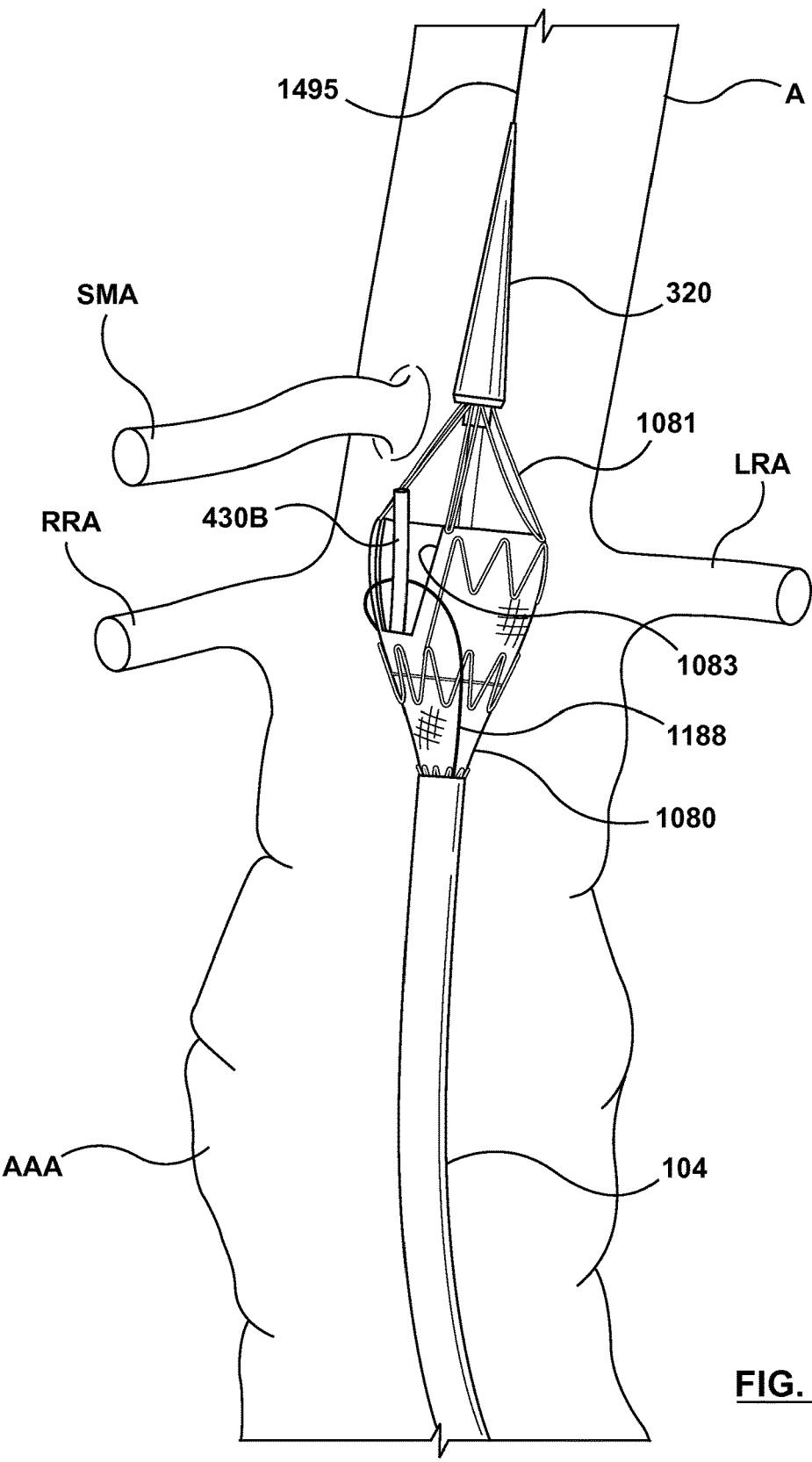
Figure 25:
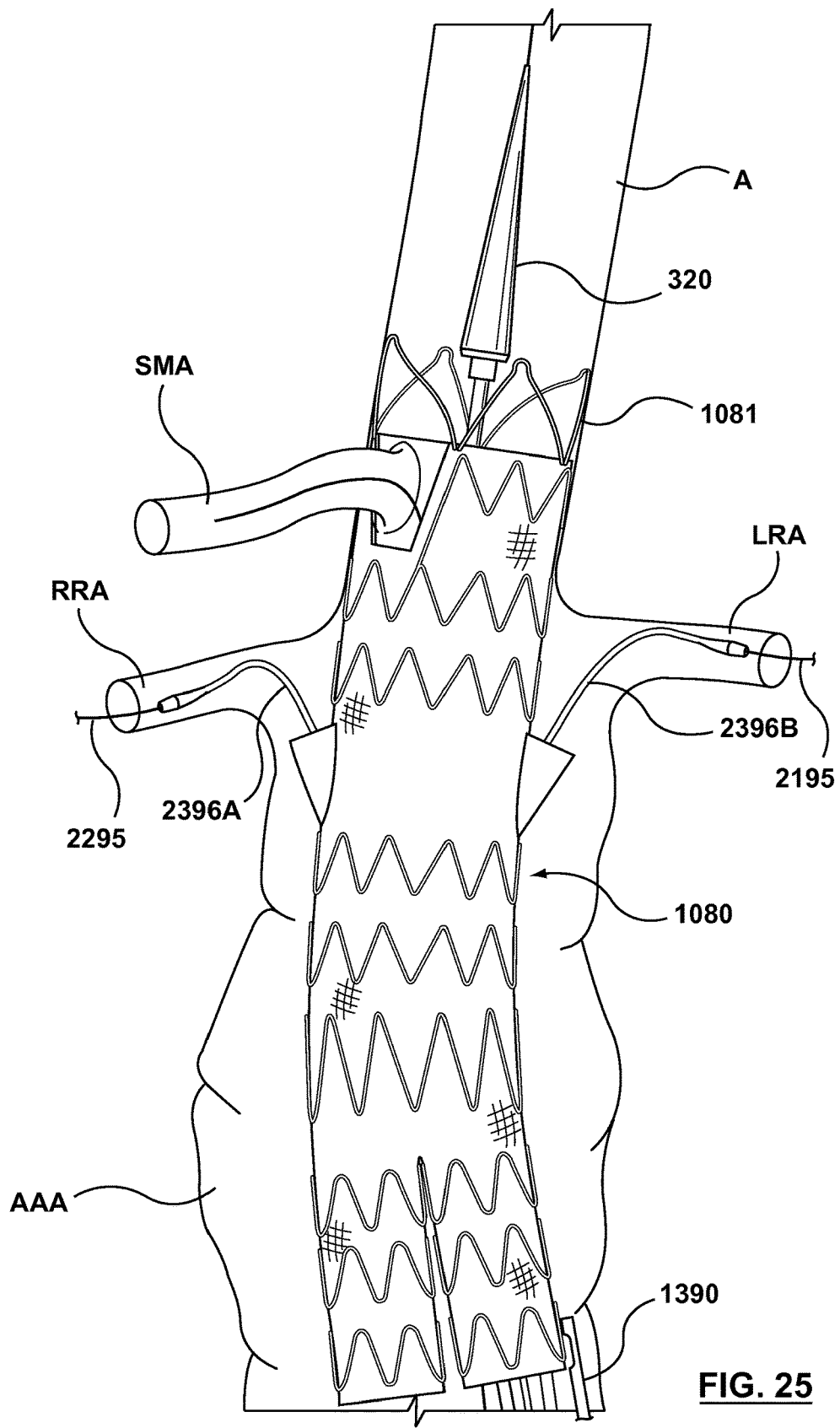

FIG. 15 depicts a first stage of the deployment of main stent-graft 1080 with a proximal portion of main stent-graft 1080 released from sheath component 104 to below vessel lumen cut-out 1083, which also exposes the distal end of elongate guidewire tube 430B. As discussed in detail above, sheath component 104 is distally retracted for the first stage of deployment of main stent-graft 1080 by rotating driver grip section 214 of handle component 102. Wire 1188, disposed as described above with reference to FIG. 11, is shown lifting guidewire tube 430B external of vessel lumen cut-out 1083 so as to be generally aligned with the SMA. Proximal anchor stent 1081 is held in a partially compressed state by tip capture mechanism 320 and remains in this state until full deployment of main-stent graft 1080 is desired, as shown in FIG. 25.

Figure 16:
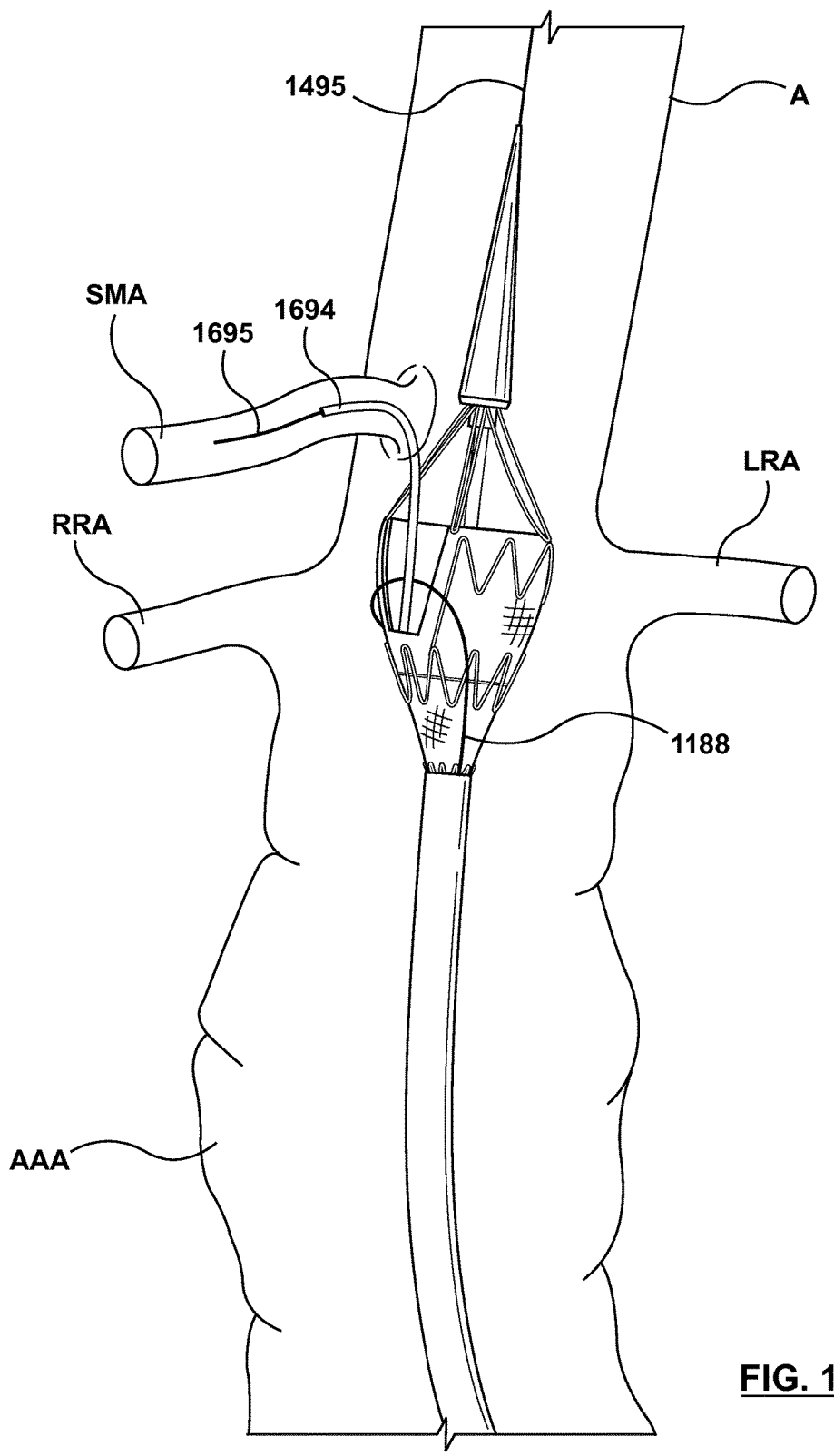
Figure 17:
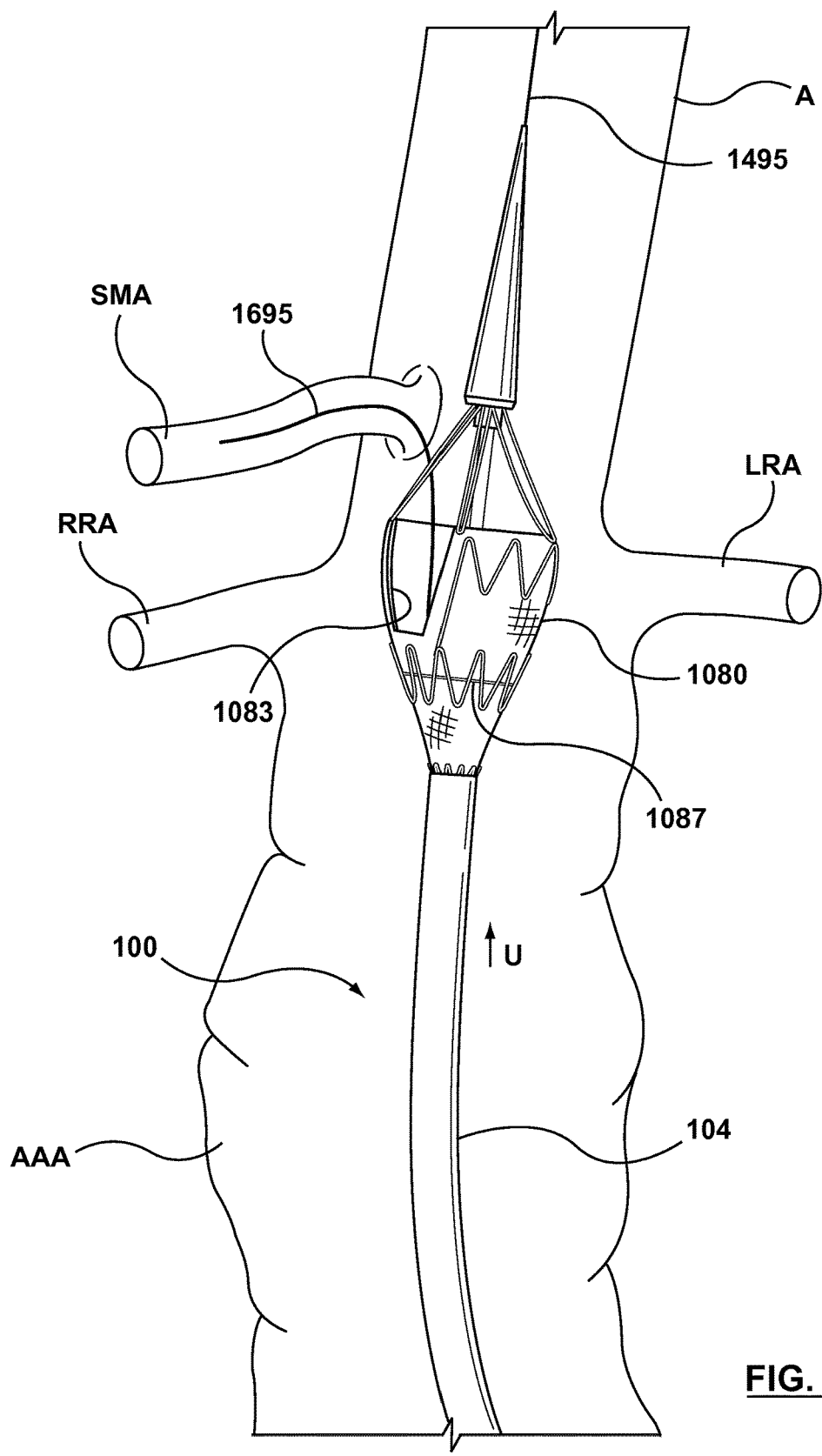
Figure 18:
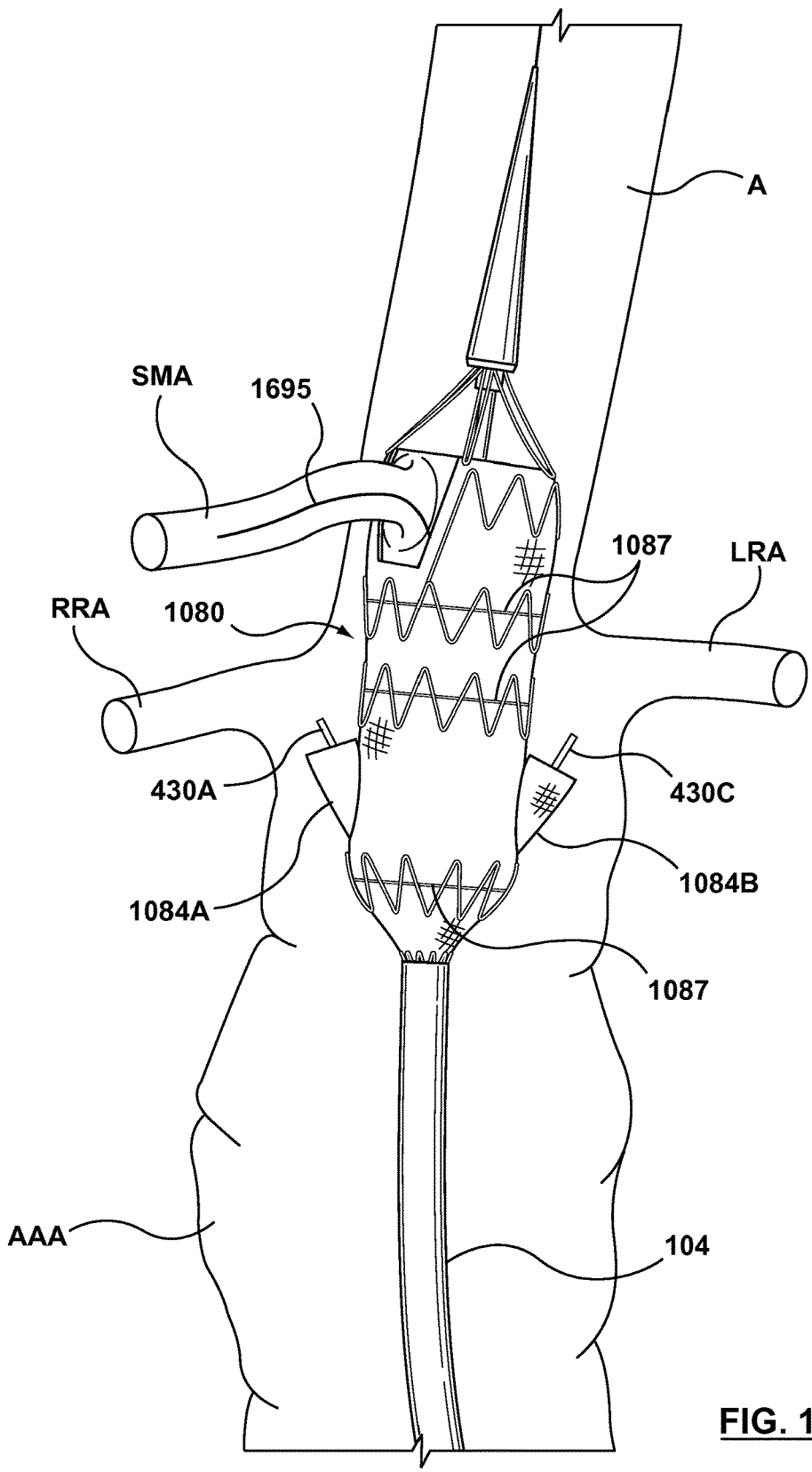

FIGS. 16 and 17 depict the cannulation of the SMA to align vessel lumen cut-out 1083 of main stent-graft 1080 with an ostium of the SMA, wherein "cannulation" and "cannulate" are terms that are used herein with reference to the navigation of a guidewire and guide catheter into a target vessel. In order to cannulate the SMA, a guidewire 1695 is inserted through guidewire tube 430B and advanced until in the thoracic aorta. Guidewire tube 430B is then removed by the physician over guidewire 1695 by pulling access port seal component 432B free of its hemostasis seal 438B and retracting removable lumen component 231B until guidewire tube 430B is free of handle component 102. A curved guide catheter 1694 is then inserted into delivery sheath port 516B and advanced over indwelling guidewire 1695 to be proximal to the SMA ostium. The guidewire 1695 and curved guide catheter 1694 are then used in conjunction via manipulation by the operator to cannulate the vessel, as shown in FIG. 16. At this time wire 1188 is removed by pulling pull ring 1189 until wire 1188 is free of access port seal component 432A of removable lumen component 231A. Similarly, guide catheter 1694 is removed from delivery system 100 by proximally retracting guide catheter 1694 through hemostasis seal 438B and delivery sheath port 516B defined thereby until the guide catheter is free of handle component 102. Delivery system 100 is then advanced in the direction of arrow U until vessel lumen cut-out 1083 frames or aligns with the ostium of the SMA, as shown in FIG. 18. Guidewire 1695 remains positioned through the SMA during the remaining deployment steps in order to maintain positioning and alignment of main stent-graft 1080. In an alternate embodiment, guide catheter 1694 remains disposed over guidewire 1695 so that together the devices are positioned through the SMA during the remaining deployment steps in order to maintain positioning and alignment of main stent-graft 1080.

FIG. 18 depicts a second stage of the deployment of main stent-graft 1080 with main stent-graft 1080 having been released from sheath component 104 to below first and second branch graft couplings 1084A, 1084B, which also exposes the distal ends of elongate guidewire tubes 430A, 430C to be generally aligned with renal arteries RRA, LRA, respectively. As discussed in detail above, sheath component 104 is distally retracted for the second stage of deployment of main stent-graft 1080 by rotating driver grip section 214 of handle component 102.

Figure 19:
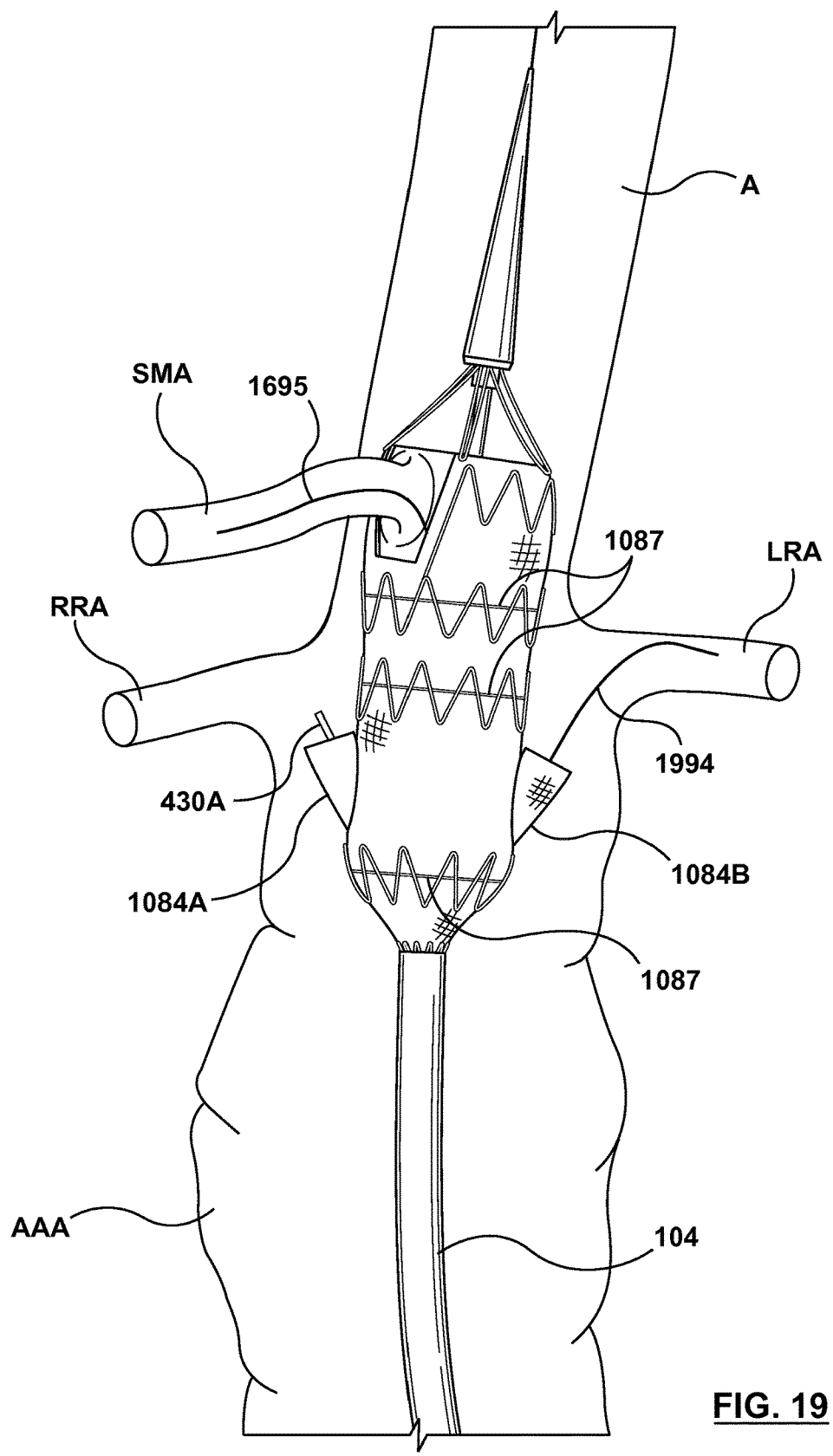
Figure 20:
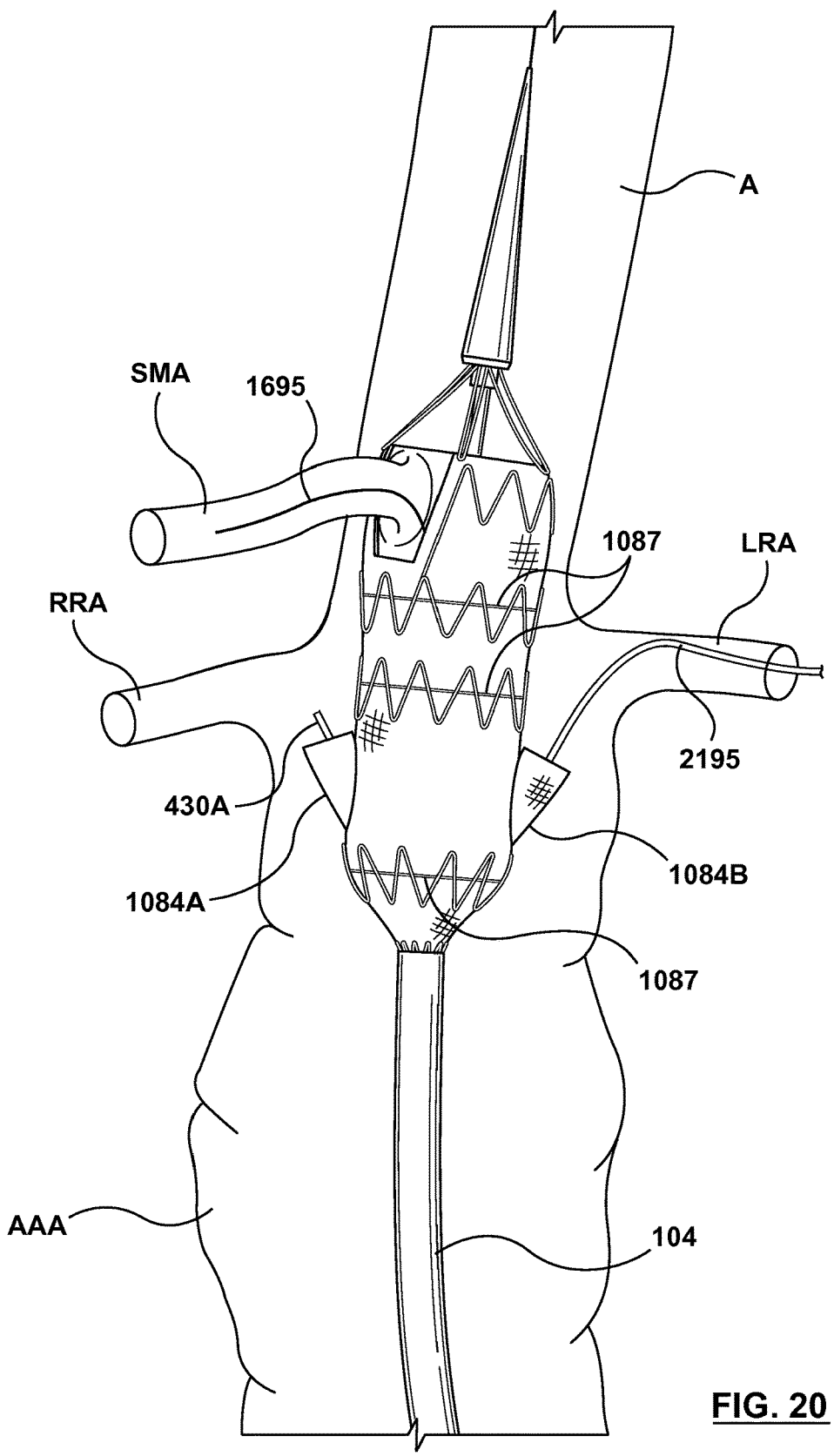
Figure 21:
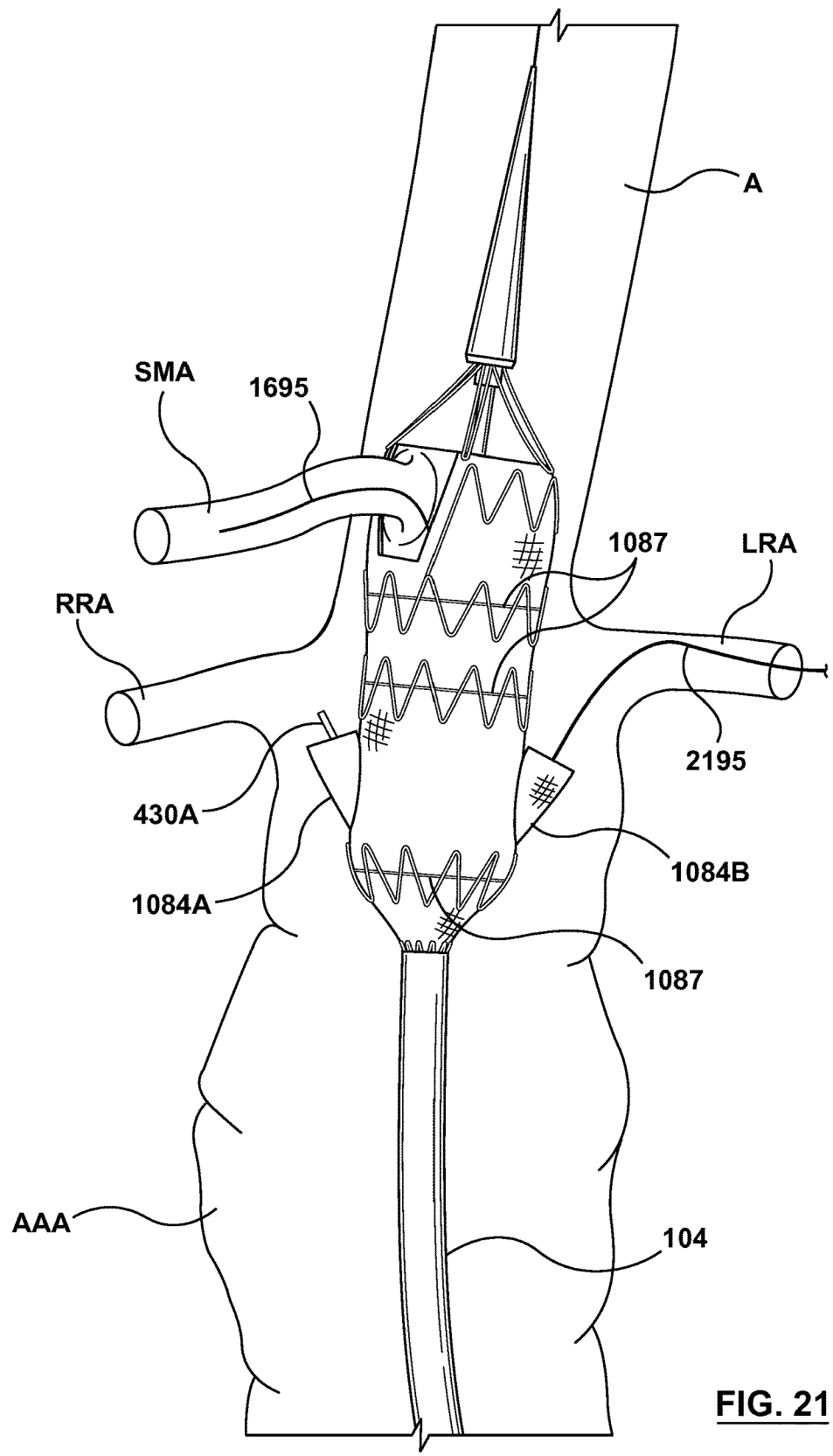
Figure 22:
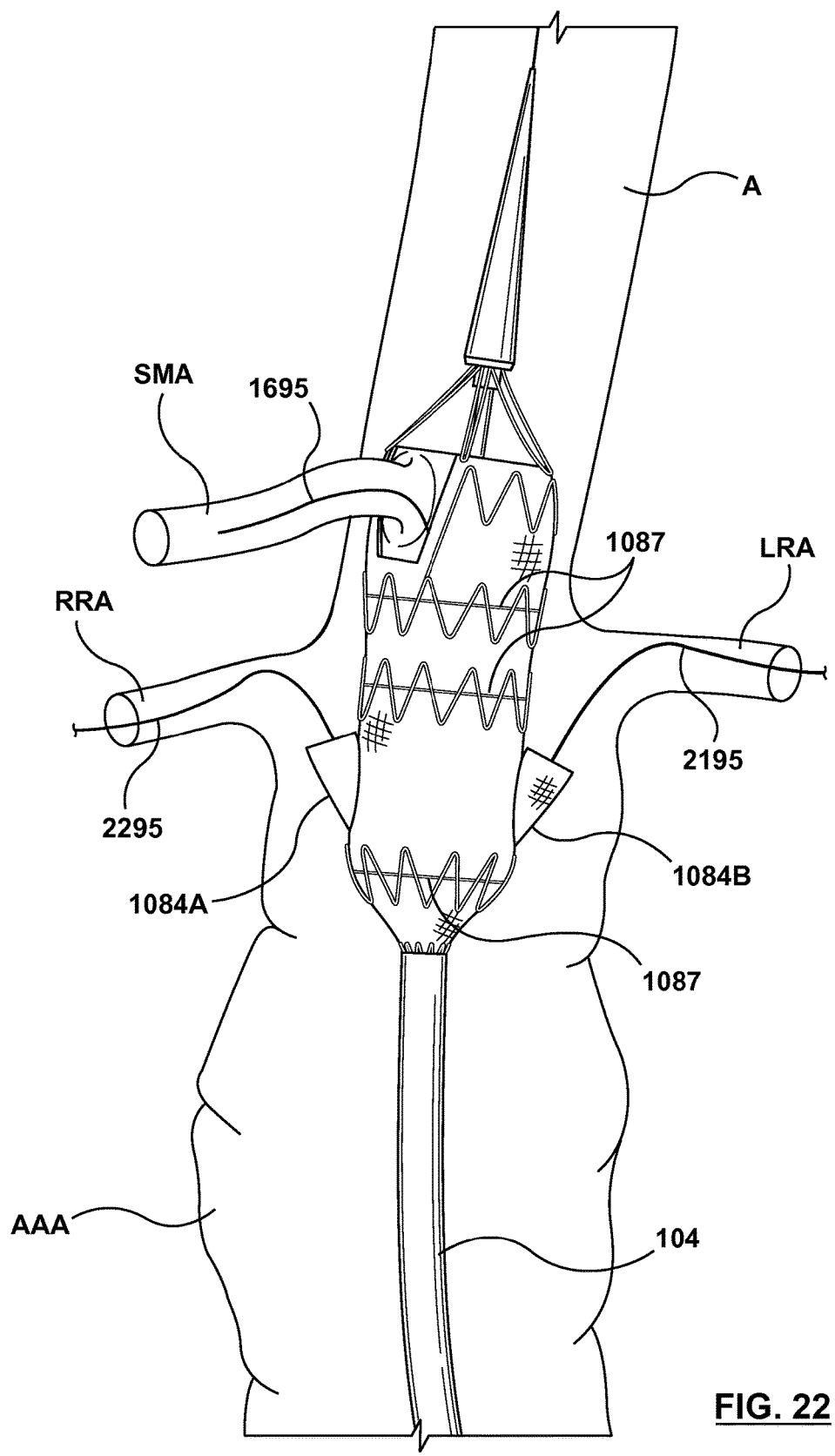

FIGS. 19-22 depict the cannulation of the RRA and LRA to align branch graft couplings 1084A, 1084B with the ostium of renal arteries RRA, LRA, respectively, and thereby finalize the positioning of main stent-graft 1080 at the treatment site while still only partially released or deployed from sheath component 104 of delivery system 100. Initially a wire 1994 is delivered through guidewire tube 430C of delivery system 100 and tracked into the ostium of the LRA, as shown in FIG. 19, and guidewire tube 430C is then removed from delivery system 100 by pulling access port seal component 432C free of its hemostasis seal and retracting removable lumen component 231C until guidewire tube 430C is free of handle component 102. Thereafter as shown in FIG. 20, a tubular sheath or guide catheter 2094 is advanced over wire 1994 to extend within the LRA, after having been inserted through an associated delivery sheath port 516C of handle component 102, and wire 1994 is then removed via delivery sheath port 516C. A guidewire 2195 is tracked through a lumen of sheath 2094 until it extends within the LRA, at which point sheath 2094 is removed from delivery system 100 by proximally retracting sheath 2094 through hemostasis seal 438C and delivery sheath port 516C defined thereby until the guide catheter is free of handle component 102, as represented in FIG. 21. The steps described for cannulating the LRA are then repeated to cannulating the RRA, which is shown in FIG. 22 after the final step of withdrawing a tubular sheath or guide catheter has been performed such that guidewire 2295 is left indwelling within the RRA. In another embodiment, the RRA may be cannulated prior to the LRA or the cannulation steps may be performed for both the RRA and the LRA concurrently.

Figure 23:
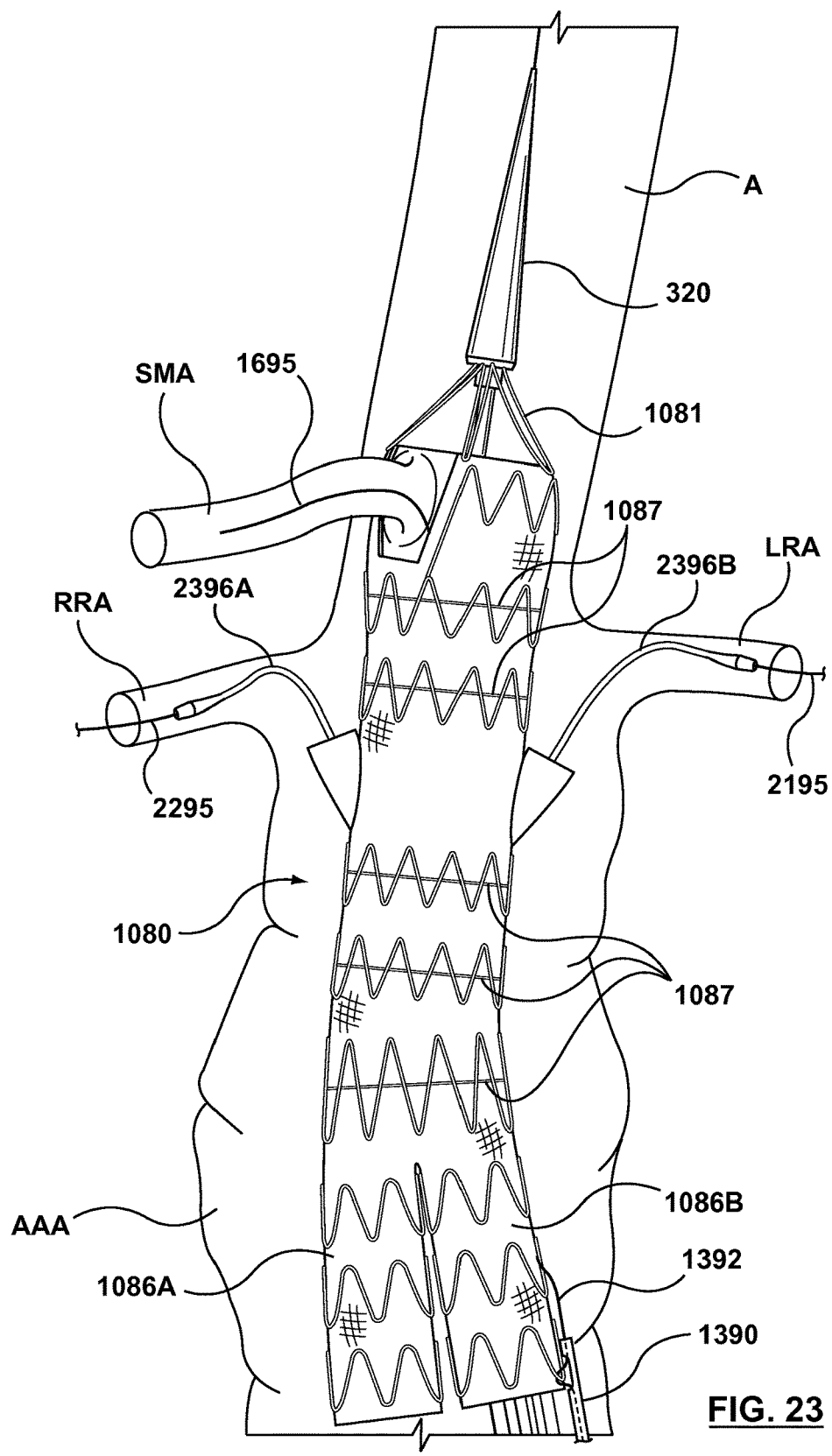

FIG. 23 depicts a third stage of the deployment of main stent-graft 1080 with main stent-graft 1080 having been fully released from sheath component 104. As discussed in detail above, sheath component 104 is distally retracted for the third stage of deployment of main stent-graft 1080 by rotating driver grip section 214 of handle component 102. Main stent-graft 1080 remains only partially expanded or deployed due to circumferentially constraining sutures 1087 and proximal anchor stent 1081 being held in a partially compressed state by tip capture mechanism 320. A distal end of main stent-graft 1080 is held by the interaction of trigger wire 1392 and distal stent graft capture tube 1390 as described above with reference to FIGS. 13 and 13A.

Although not shown in FIG. 23, middle member component 233 has been removed in order to reconfigure delivery system 100 into its delivery sheath configuration such that lumen 105 of sheath component 104 is essentially free of obstruction. Middle member component 233 is removed from delivery system 100 by pulling middle member handle 442 free of hemostasis seal 445 and retracting middle member shaft 446 until it is free of handle component 102. After removal of middle member component 233, a branch delivery catheter 2396A is advance through delivery sheath port 516A of handle component 102 over guidewire 2295 that lies therethrough until a distal end of branch delivery catheter 2396A has been positioned within the RRA and a branch delivery catheter 2396C is advance through delivery sheath port 516C of handle component 102 over guidewire 2195 that lies therethrough until a distal end of branch delivery catheter 2396C has been positioned within the LRA. For use in embodiments hereof, branch delivery catheters 2396A, 2396B may be a stent-graft delivery system similar to that used to deliver the Complete SE stent from Medtronic, Inc. or any other comparable delivery system.

Figure 24:
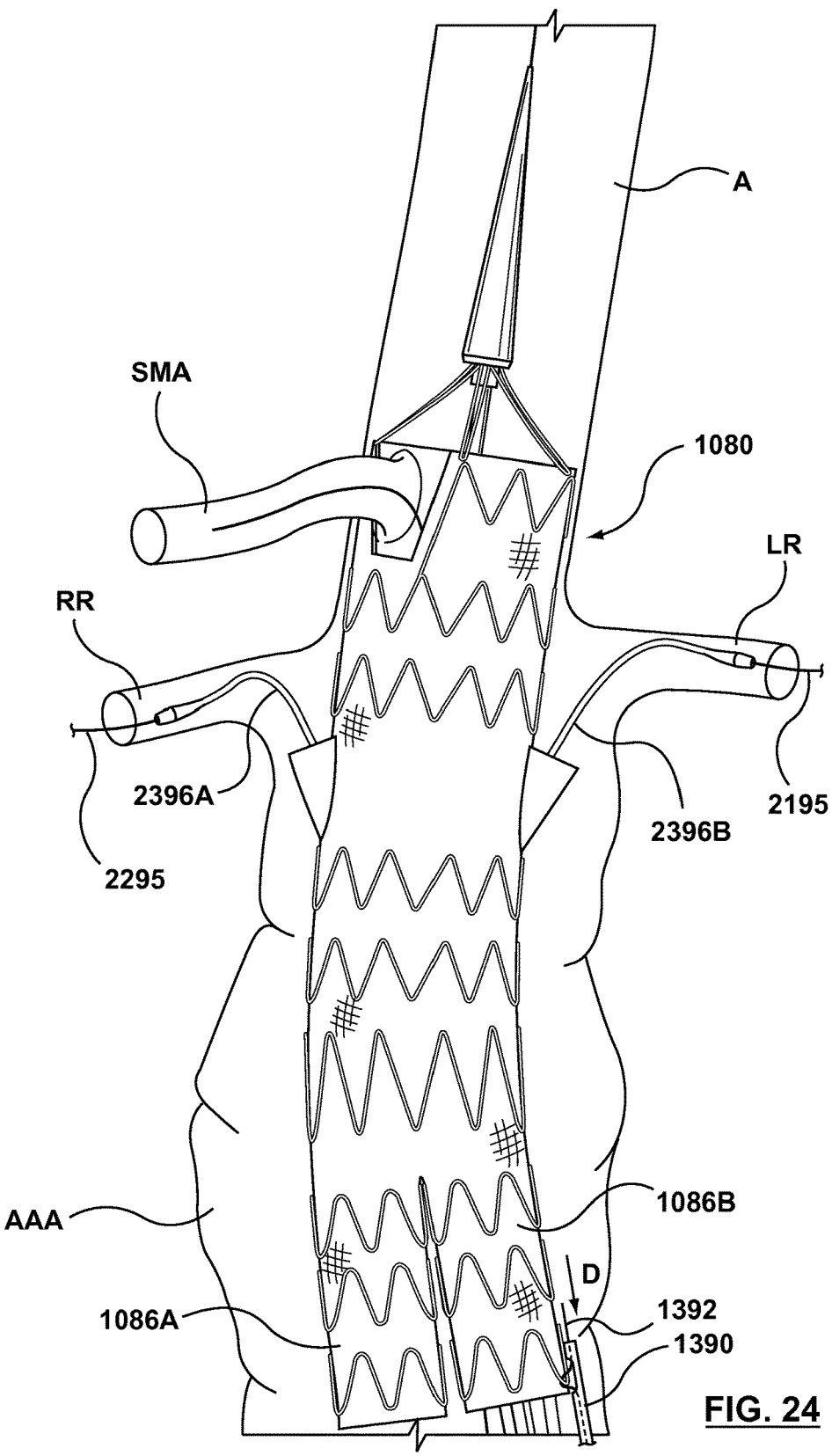

FIG. 24 depicts main stent-graft 1080 in a fourth stage of deployment after trigger wire 1392 has been proximally retracted in the direction of arrow D to release circumferentially constraining sutures 1087 such that the self-expanding stents of main stent-graft 1080, other than proximal anchor stent 1081, are permitted to return to their fully expanded configurations. Trigger wire 1392 is completely removed in one motion from handle component 102 by an operator, which releases the circumferentially constraining sutures 1087 as well as second leg 1086B of main-stent graft 1080 to complete the fourth stage of deployment. As discussed above with reference to FIGS. 1B and 12, trigger wire pull tab 109 is pulled outwardly from handle component 102 to disengage inwardly extending catch 109' from tip release safety lock 107 and then pulled proximally by an operator to free trigger wire 1392 of circumferentially constraining sutures 1087 and distal stent graft capture tube 1390. The release of tip release safety lock 107 allows the operator to rotate tip release section 208 of handle component 102 and activate tip capture mechanism 320 to thereby release self-expanding proximal anchor stent 1081 into apposition with the aorta, whereby main stent-graft 1080 is in its final stage of deployment or in other words is in a fully deployed or expanded configuration free of delivery system 100 as shown in FIG. 25.

Figure 26:
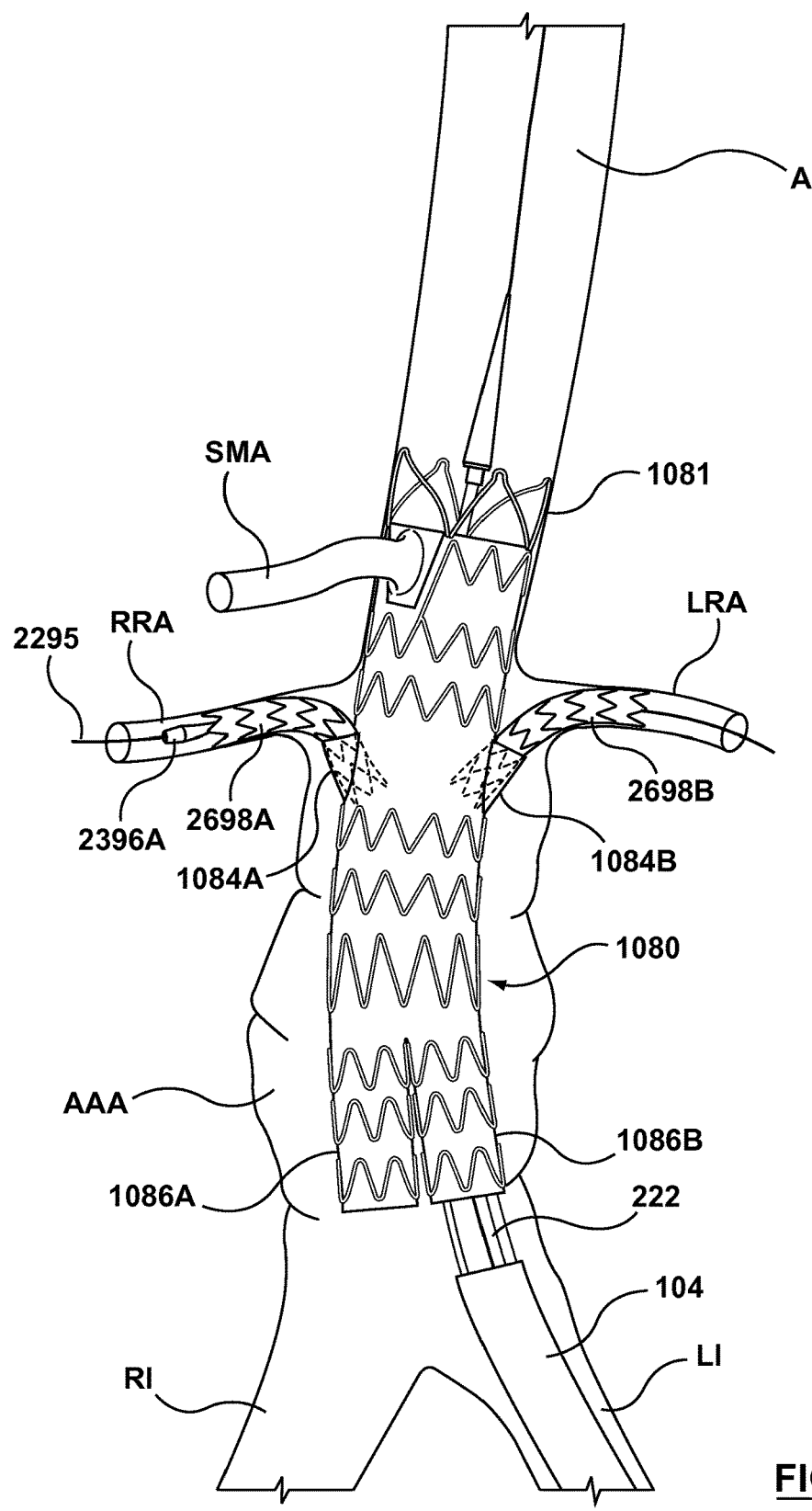

FIG. 26 depicts branch stent-grafts 2698A, 2698B released from their respective branch delivery catheters 2396A, 2396B so that each is deployed to extend from its respective renal artery RRA, LLR into and through its respective branch graft coupling 1084A, 1084B of main stent-graft 1080 to be anchored therein and to provide respective fluid passageways therebetween. For use in embodiments hereof, branch stent-grafts 2698A, 2698B are tubes of graft material having self-expanding stent support structures and may be a tubular stent-graft such as tubular stent-grafts suitable as limbs for use in the ENDURANT® stent graft system available from Medtronic, Inc. After deployment of branch stent-grafts 2698A, 2698B, branch delivery catheters 2396A, 2396B and delivery system 100 are withdrawn from the vasculature.

Figure 27:
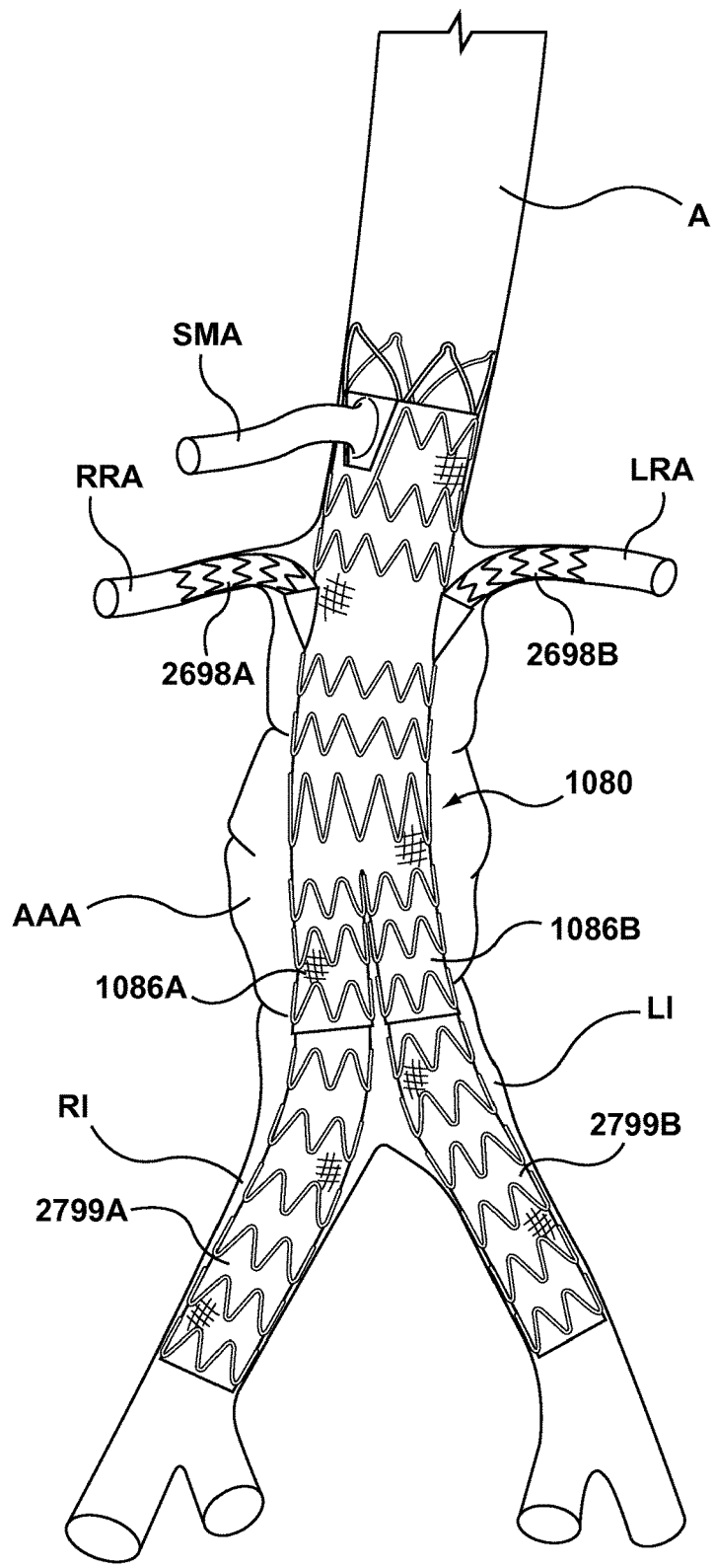

FIG. 27 depicts main stent-graft 1080 coupled to limb stent-grafts 2799A, 2799B, which have been introduced and deployed so that each extends from its respective leg 1086A, 1086B of main stent-graft 1080 to its respective iliac artery RI, LI to be anchored therein and to provide respective fluid passageways therebetween. For use in embodiments hereof, limb stent-grafts 2799A, 2799B are tubes of graft material having self-expanding stent support structures and may be a tubular stent-graft similar to an ENDURANT® type of stent-graft available from Medtronic, Inc. that is delivered and deployed by a delivery system similar to the ENDURANT® stent-graft delivery system also available from Medtronic, Inc.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A reconfigurable porting structure for a stent-graft delivery system comprising:
    an internal seal component defining an inner access port therethrough, the internal seal component being fixedly attached to a handle component of the stent-graft delivery system; and
    a removable lumen component including
        an external seal component including a seal portion defining an outer access port therethrough and a tubular coupling portion that distally extends directly from the seal portion, wherein the tubular coupling portion has an outer diameter sized to permit the tubular coupling portion to slide within the inner access port to removably couple the external seal component to the internal seal component, and
        an elongate guidewire tube having a proximal portion and an elongate distal portion, the proximal portion being secured within the tubular coupling portion of the external seal component with a proximal end of the proximal portion being disposed distal of the seal portion of the external seal component to be aligned with the outer access port for permitting introduction of a guidewire from the outer access port into a lumen of the guidewire tube, and the elongate guidewire tube being disposed to extend with the tubular coupling portion through the inner access port of the internal seal component when the external and internal seal components are coupled to each other,
    wherein when the removable lumen component and internal seal component are coupled to each other the outer access port is configured to maintain hemostasis with a guidewire extending therethrough, and the elongate distal portion of the elongate guidewire tube extends from the internal seal component to a lumen of the stent-graft delivery system, and
    wherein when the removable lumen component is removed from the internal seal component, the inner access port is configured to maintain hemostasis with a stent-graft delivery system extending therethrough.

2. The porting structure of claim 1, wherein the tubular coupling portion defines a guidewire passageway therethrough that distally extends from the outer access port.

3. The porting structure of claim 1, wherein a lumen of the guidewire tube extends from the outer access port for receiving a guidewire therethrough.

4. The porting structure of claim 1, wherein the external seal component with the guidewire tube attached thereto are removably coupled to the handle component via the internal seal component.

5. The porting structure of claim 1, further comprising:
    a removable access port dilator for engaging with and dilating the outer access port of the external seal component, wherein the access port dilator defines a lumen through which a guidewire is tracked to be inserted through the outer access port.

6. The porting structure of claim 5, wherein the access port dilator includes a reduced-diameter male portion that slides within the outer access port to dilate a molded hole that forms the outer access port.

7. The porting structure of claim 1, wherein the inner access port is sized to receive up to a 13 French medical device therethrough when the removable lumen component is removed from the internal seal component.

8. The porting structure of claim 1, wherein the tubular coupling portion engages the internal seal component with a snap fit engagement.

9. The porting structure of claim 8, wherein the tubular coupling portion includes a reduced diameter portion smaller than the outer diameter.

10. A reconfigurable porting structure for a stent-graft delivery system comprising:
    an internal seal component defining an inner access port therethrough, wherein the inner access port forms an opening of the internal seal component; and
    an external seal component having a seal portion that defines an outer access port therethrough and having a tubular coupling portion that distally extends directly from the seal portion, wherein the tubular coupling portion has an outer diameter sized to permit the tubular coupling portion to slide within the opening formed by the inner access port of the internal seal component and to have a frictional or interference fit therewith for removably coupling the internal and external seal components together,
    wherein the internal seal component is fixedly attached to a handle component of the stent-graft delivery system such that the external seal component is removably coupled to the handle component solely by engagement between the tubular coupling portion and the internal seal component,
    wherein when the external and internal seal components are coupled to each other the outer access port is configured to maintain hemostasis with a guidewire extending therethrough, and
    wherein when the external seal component is removed from the internal seal component the inner access port is configured to maintain hemostasis with a stent-graft delivery system extending therethrough.

11. The porting structure of claim 10, wherein the inner access port is sized to receive up to a 13 French medical device therethrough when the external seal component is removed from the internal seal component.

12. The porting structure of claim 10, wherein an elongate guidewire tube is attached to the external seal component such that a lumen of the guidewire tube extends from the outer access port for receiving a guidewire therethrough.

13. The porting structure of claim 12, wherein the guidewire tube passes through the internal seal component when the internal and external seal components are coupled together.

14. The porting structure of claim 13, wherein the external seal component with attached guidewire tube are removably coupled to the handle component via the internal seal component.

15. The porting structure of claim 10, wherein the tubular coupling portion engages the internal seal component with a snap fit engagement.

16. The porting structure of claim 15, wherein the tubular coupling portion includes a reduced diameter portion smaller than the outer diameter.

17. A reconfigurable porting structure for a stent-graft delivery system comprising:
an internal seal component defining an inner access port therethrough, wherein the inner access port forms an opening of the internal seal component;
an external seal component having a seal portion that defines an outer access port therethrough and having a tubular coupling portion that distally extends directly from the seal portion, wherein the tubular coupling portion has an outer diameter sized to permit the tubular coupling portion to slide within the opening formed by the inner access port of the internal seal component and to have a frictional or interference fit therewith for removably coupling the internal and external seal components together,
wherein the internal seal component is fixedly attached to a handle component of the stent-graft delivery system such that the external seal component is removably coupled to the handle component solely by engagement between the tubular coupling portion and the internal seal component; and
a removable access port dilator for engaging with and dilating the outer access port of the external seal component, wherein the access port dilator defines a lumen through which a guidewire is tracked to be inserted through the outer access port.

18. The porting structure of claim 17, wherein the access port dilator includes a reduced-diameter male portion that slides within the outer access port to dilate a molded hole that forms the outer access port.

* * * * *